(12) United States Patent
Di Santo et al.

(10) Patent No.: US 7,776,883 B2
(45) Date of Patent: Aug. 17, 2010

(54) QUINOLIN-4-ONES AS INHIBITORS OF RETROVIRAL INTEGRASE FOR THE TREATMENT OF HIV, AIDS AND AIDS RELATED COMPLEX (ARC)

(75) Inventors: Roberto Di Santo, Rome (IT); Yves Pommier, Bethesda, MD (US); Christophe Marchand, Bethesda, MD (US); Marino Artico, Rome (IT); Roberta Costi, Rome (IT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 991 days.

(21) Appl. No.: 10/591,679

(22) PCT Filed: Mar. 9, 2005

(86) PCT No.: PCT/US2005/008202

§ 371 (c)(1),
(2), (4) Date: Sep. 1, 2006

(87) PCT Pub. No.: WO2004/046115

PCT Pub. Date: Jun. 3, 2004

(65) Prior Publication Data

US 2007/0219242 A1    Sep. 20, 2007

Related U.S. Application Data

(60) Provisional application No. 60/552,423, filed on Mar. 10, 2004.

(51) Int. Cl.
C07D 215/38 (2006.01)
A61K 31/04 (2006.01)

(52) U.S. Cl. .................. 514/314; 546/159; 546/167
(58) Field of Classification Search ............ 546/159, 546/167; 514/314

See application file for complete search history.

(56) References Cited

U.S. PATENT DOCUMENTS

| 4,386,092 | A | 5/1983 | Oe et al. |
| 5,217,972 | A | 6/1993 | Grohe et al. |
| 5,519,016 | A | 5/1996 | Kimura et al. |
| 6,982,091 | B2 * | 1/2006 | Pauletti et al. ............. 424/430 |

FOREIGN PATENT DOCUMENTS

| EP | 0 8780194 A1 | 11/1998 |
| WO | WO 99/50245 | 10/1999 |
| WO | WO 99/62513 | 12/1999 |
| WO | WO 99/62520 | 12/1999 |
| WO | WO 99/62897 | 12/1999 |
| WO | WO 00/06529 | 2/2000 |
| WO | WO 01/00578 A1 | 1/2001 |
| WO | WO 01/98248 A2 | 12/2001 |
| WO | WO 03/049695 A2 | 6/2003 |
| WO | WO 2004/046115 A1 | 6/2004 |

OTHER PUBLICATIONS

Baba et al., "Potent and Selective Inhibition of Human Immunodeficiency Virus Type 1 Transcription by Piperazinyloxoquinoline Derivatives," *Antimicrobrial Agents and Chemotherapy* 41(6):1250-1255, 1997.
Baba et al., "Inhibition of Human Immunodeficiency Virus Type 1 Replication and Cytokine Production by Fluoroquinoline Derivatives," *Molecular Pharmacology* 53:1097-1103, 1998.
De Clerq, "New developments in anti-HIV chemotherapy," *Pure Appl. Chem* 73(1):55-66, 2001.
Espeseth et al., "HIV-1 integrase inhibitors that compete with the target DNA substrate define a unique strand stransfer conformation for integrase," *PNAS* 97(21):11244-11249, 2000.
Goldgur et al., "Structure of the HIV-1 integrase catalytic domain complexed with an inhibitor: A platform for antiviral drug design," *PNAS* 96(23):13040-13043, 1999.
Grobler et al., "Diketo acid inhibitor mechanism and HIV-1 integrase: Implications for met al binding in the active side of phosphotransferase enzymes," *PNAS* 99(10):6661-6666, 2002.
Hazuda et al., "Inhibitors of Strand Transfer that Prevent Integration and Inhibit HIV-1 Replication in Cells," *Science* 287:646-650, 2000.
Marchand et al., "Structural Determinants for HIV-1 Integrase Inhibition by β-Diketo Acids," *The Journal of Biological Chemistry* 277(15):12596-12603, 2002.
Okamoto et al., "Inhibition of Human Immunodeficiency Virus Type 1 Replication by Combination of Transcription Inhibitor K-12 and Other Antiretroviral Agents in Acutely and Chronically Infected Cells," *Antimicrobial Agents and Chemotherapy* 43(3):492-497, 1999.
Okamoto et al., "Inhibition of the RNA-Dependent Transactivation and Replication of Human Immunodeficiency Virus Type 1 by a Fluoroquinoline Derivative K-37," *Virology* 272:402-408, 2000.
Pais et al., "Structure Activity of 3-Aryl-1,3-diketo-Containing Compounds as HIV-1 Integrase Inhibitors," *J. Med Chem.* 45:3184-3194, 2002.
Wai et al., "4-Aryl-2,4-dioxobutanoic Acid Inhibitors of HIV-1 Integrase and Viral Replication in Cells," *Journal of Medical Chemistry* 43(26):4923-4926, 2000.
Zhang et al., "Azido-Containing Aryl β-Diketo Acid HIV-1 Integrase Inhibitors," *Bioorganic& Medicinal Chemistry Letters* 13:1215-1219, 2003.

* cited by examiner

*Primary Examiner*—D. Margaret Seaman
(74) *Attorney, Agent, or Firm*—Klarquist Sparkman, LLP

(57) ABSTRACT

Novel quinoline inhibitors of retroviral integrase, particularly HIV-1 integrase. The quinoline inhibitors are oxoquinolines that can be used for preventing or treating AIDS or HIV infection in a subject.

42 Claims, 1 Drawing Sheet

FIG. 1   5'-GTGTGGAAAATCTCTAGCAGT-3'  A
          3'-CACACCTTTTAGAGATCGTCA-5'  B

QUINOLIN-4-ONES AS INHIBITORS OF RETROVIRAL INTEGRASE FOR THE TREATMENT OF HIV, AIDS AND AIDS RELATED COMPLEX (ARC)

RELATED APPLICATION DATA

This is a §371 U.S. National Stage of International Application No. PCT/US2005/008202, filed Mar. 9, 2005, which was published in English under PCT Article 21(2), which in turn claims the benefit of commonly owned U.S. Provisional Application No. 60/552,423, filed Mar. 10, 2004. These applications are incorporated herein by reference in their entirety.

FIELD

Disclosed herein are novel compounds as well as methods and pharmaceutical compositions for treating or preventing retrovirus infection, particularly human immunodeficiency virus (HIV) infection, in a subject.

BACKGROUND

HIV is a retrovirus that causes immunosuppression in humans, and leads to a disease complex known as acquired immunodeficiency syndrome (AIDS). HIV disease is characterized by progressive functional deterioration of the immune system. The treatment of HIV disease has been significantly advanced by the recognition that combining different drugs with specific activities against different biochemical functions of the virus can help reduce the rapid development of drug resistant viruses that were seen in response to single drug treatment. However, even with combined treatments, multi-drug resistant strains of the virus have emerged. There is therefore a continuing need for the development of new antiretroviral drugs that act specifically at different steps of the viral infection and replication cycle.

The integrase (IN) enzyme is an example of such a specific target. This enzyme catalyzes the insertion by virally-encoded integrase of proviral DNA into the host cell genome, which is the mechanism by which HIV and other retroviruses are introduced into human T-lymphoid cells. For HIV-1, this process is mediated by a 32 kD virally encoded integrase, having conserved sequences in the HIV long terminal repeats (LTR). Integration is believed to be mediated by integrase in three steps. The first, assembly, produces a stable nucleoprotein complex with viral DNA sequences via reverse-transcription in the cytoplasm of infected cells. Integrase then cleaves two nucleotides from each of the 3' termini of the linear viral DNA ends which contain a highly conserved CA motif. The third step, strand transfer, involves covalently joining the recessed 3' OH termini of the viral DNA at a staggered cut made at the host target site. The cleaved DNA migrates to the nucleus as a part of a large nucleoprotein complex, where the integrase catalyzes the insertion of viral DNA into a host chromosome by a direct transesterification reaction.

In vitro assays have previously been developed to identify integrase inhibitors (see, e.g., Mazumder et al. "Retroviral Integrase: A Novel Target in Antiviral Development; Basic In Vitro Assays with the Purified Enzyme," in: *Antiviral Methods and Protocols*, Kinchington et al., Ed.; The Humana Press, Inc.: Totowa, N.J., 1999, pp. 327-335; Marchand et al., "In vitro human immunodeficiency virus type I integrase assays," *Methods Enzymol.* 340: 624-633, 2001; and Chow, S. A., "In vitro assays for activities of retroviral integrase," *Methods* 12:306-17, 1997), and have permitted the discovery of diverse classes of drugs that inhibit integrase (see, e.g., Pommier et al., "HIV-1 integrase as a target for antiviral drugs," *Antiviral Chem Chemother* 8:483-503, 1997; Neamati et al., "Design and discovery of HIV-1 integrase inhibitors," *Drug Discovery Today* 2:487-498, 1997). However, the drugs discovered by these assays have not been highly selective and potent inhibitors of the integrase enzyme. Many of these drugs have additionally been non-selective inhibitors of reverse transcriptase or HIV protease, which limits their usefulness in combination therapy directed to different specific steps of the retroviral life cycle. Moreover, a significant number of patients fail to respond to treatments with reverse transcriptase or HIV protease inhibitors, and viral resistance remains a major problem. Hence, there exists a need for integrase inhibitors that can be useful for acquired immune deficiency syndrome (AIDS) therapy.

SUMMARY

Disclosed herein are novel compounds of the following formula (I), or tautomers or pharmaceutically acceptable salts thereof:

wherein $R_1$ is selected from —H, —$C_{1-6}$ alkyl, or —$C_{1-6}$ alkyl substituted with $R_7$;

Z is selected from —C(O)O$R_2$ or —C(O)CH$_2$C(O)X;

X is selected from:
(a) -a 5 or 6-membered aromatic or heteroaromatic ring, containing 0, 1, 2, 3 or 4 heteroatoms selected from oxygen, nitrogen and sulfur, unsubstituted or independently substituted on a nitrogen or carbon atom by at least one substituent selected from halogen, $C_{1-6}$ alkyl, or phenyl, or
(b) —C(O)O$R_2$;

$R_2$ is selected from —H or —$C_{1-6}$ alkyl;

$R_3$, $R_4$, $R_5$ and $R_6$ are each independently selected from —H, -halogen, —$C_{1-6}$ alkyloxy-, —N($R_8$)($R_9$), —C(O)CH$_3$, —C(O)CH$_2$C(O)X, —S(O)$_n$—$R_{10}$ wherein n is independently selected from 0, 1 and 2, heteroalkyl, cycloalkyl, substituted cycloalkyl, heterocycloalkyl, substituted heterocycloalkyl, aryl, substituted aryl, heteroaryl, or substituted heteroaryl;

$R_7$ is selected from heteroalkyl, cycloalkyl, substituted cycloalkyl, heterocycloalkyl, substituted heterocycloalkyl, aryl, substituted aryl, heteroaryl, or substituted heteroaryl;

each $R_8$ and $R_9$ is independently selected from —H or —$C_{1-2}$ alkyl; and each $R_{10}$ is independently selected from —$C_{1-6}$ alkyl, pyridyl, or phenyl, wherein the phenyl is unsubstituted or substituted on a carbon atom by least one substituent selected from halogen, —CH$_3$, —O$R_2$, or —NO$_2$;

provided that if Z is —C(O)O$R_2$ then at least one of $R_3$, $R_4$, $R_5$ or $R_6$ is —C(O)CH$_2$C(O)X.

The compounds of formula (I) that are disclosed herein have been found to exhibit anti-HIV integrase activity.

Also disclosed herein is a pharmaceutical composition that includes the formula (I) compound and a pharmaceutically acceptable carrier.

The formula (I) compounds or pharmaceutical compositions disclosed herein can be used in a method of treating or preventing AIDS or HIV infection in a subject that involves administering to the subject a therapeutically effective amount of the formula (I) compound or pharmaceutical composition.

The formula (I) compounds also can be used in a method of inhibiting a retroviral integrase that involves exposing the HIV integrase to an integrase inhibiting amount of the formula (I) compound.

This disclosure also includes a method of screening for an anti-HIV integrase drug that includes providing an assay of HIV integrase inhibition, and using the assay to screen for drugs comprising analogs or derivatives of any of the formula (I) compounds.

DETAILED DESCRIPTION OF SEVERAL EXAMPLES

For ease of understanding, the following terms used herein are described below in more detail:

"Ac" represents acetyl.

"Alkoxy" refers to an —OZ radical wherein Z is selected from alkyl, substituted alkyl, cycloalkyl, substituted cycloalkyl, heterocycloalkyl, substituted heterocycloalkyl, and combinations thereof. Illustrative alkoxy radicals include methoxy, ethoxy, benzyloxy, and t-butoxy. A related term is "aryloxy" wherein Z is selected from aryl, substituted aryl, heteroaryl, substituted heteroaryl, and combinations thereof. Illustrative alkoxy radicals include phenoxy, substituted phenoxy, 2-pyridinoxy, 8-quinalinoxy, and the like.

"Alkyl" refers to a cyclic, branched, or straight chain alkyl group containing only carbon and hydrogen, and unless otherwise mentioned typically contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents as described below.

"Amino" refers to the group —$NZ^1Z^2$ wherein each of $Z^1$ and $Z^2$ is independently selected from hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, and combinations thereof.

An "animal" is a living multicellular vertebrate organism, a category that includes, for example, mammals and birds. A "mammal" includes both human and non-human mammals. "Subject" includes both human and animal subjects.

"Aryl" refers to an aromatic substituent that may be a single aromatic ring or multiple aromatic rings that are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular examples, aryls have between 1 and 20 carbon atoms.

"Cycloalkyl" refers to a saturated or unsaturated cyclic non-aromatic hydrocarbon radical having a single ring or multiple condensed rings. Illustrative cycloalkyls include cyclopentyl, cyclohexyl, bicyclooctyl, and the like.

"EDT-$H_2O$" represents ethylene dithiol-water (1:1).

"Et" represents ethyl.

"Halogen" refers to fluoro, bromo, chloro and iodo substituents.

"Heteroalkyl" refers to an alkyl as described above in which one or more hydrogen or carbon atom of the alkyl is replaced by a heteroatom such as N, O, P, B or S. An alkyl substituted with a heterocycloalkyl, substituted heterocycloalkyl, heteroaryl, substituted heteroaryl, alkoxy, aryloxy or amino is included within "heteroalkyl." Illustrative heteroalkyls include cyano, benzoyl, 2-pyridyl, 2-furyl, and the like.

"Heteroaryl" refers to aromatic rings in which one or more carbon atoms of the aromatic ring(s) are replaced by a heteroatom(s) such as N, O, P, B or S. Heteroaryl refers to structures that may be a single aromatic ring, multiple aromatic rings or one or more aromatic rings coupled to one or more nonaromatic rings. Illustrative heteroaryls include, for example, thiophene, pyridine, isoxazole, phthalimide, pyrazole, indole, furan, and the like.

"Heterocycloalkyl" refers to a cycloalkyl radical as described above in which one or more of the carbon atoms of the cyclic radical is replaced by a heteroatom such as N, O, P, B or S. Illustrative heterocycloalkyls include, for example, piperazinyl, morpholinyl, tetrahydropyranyl, tetrahydrofuranyl, piperidinyl, pyrrolindinyl, oxazolinyl, and the like.

"HPLC" refers to high pressure liquid chromatography.

"KHMDS" represents potassium bis(trimethyl-silyl)amide.

"LHMDS" represents lithium bis(trimethyl-silyl)amide.

"Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002).

A "pharmaceutical agent" or "drug" refers to a chemical compound or composition capable of inducing a desired therapeutic or prophylactic effect when properly administered to a subject.

"Saline" refers to an aqueous saturated sodium chloride solution.

"sat." is saturated.

"SDS" represents sodium dodecyl sulfate.

"Substituted alkyl" refers to an alkyl as described above in which one or more hydrogen or carbon atom of the alkyl is replaced by another group such as a halogen, aryl, substituted aryl, cycloalkyl, substituted cycloalkyl, and combinations thereof. Illustrative substituted alkyls include benzyl, trichloromethyl, and the like.

"Substituted aryl" refers to an aryl radical as described above in which one or more hydrogen atom is replaced by one or more functional groups such as alkyl, substituted alkyl, cycloalkyl, substituted cycloalkyl, heterocycloalkyl, substituted heterocycloalkyl, halogen, alkylhalos, hydroxy, amino, alkoxy, and thio. Illustrative substituted aryls include chlorophenyl, 3,5-dimethylphenyl, 2,6-diisopropylphenyl, and the like.

"Substituted cycloalkyl" refers to cycloalkyl as described above in which one or more hydrogen or carbon atom is replaced by another group such as a halogen, aryl, substituted aryl, alkoxy, aryloxy, amino, and combinations thereof.

"Substituted heteroaryl" refers to a heteroaryl radical as described above in which one or more hydrogen or carbon atom is replaced by one or more functional groups such as alkyl, substituted alkyl, cycloalkyl, substituted cycloalkyl, heterocycloalkyl, substituted heterocycloalkyl, halogen, alkylhalos, hydroxy, amino, alkoxy, and thio.

"Substituted heterocycloalkyl" refers to a heterocycloalkyl radical as described above in which one or more hydrogen or carbon atom is replaced by another group such as a halogen, aryl, substituted aryl, alkoxy, aryloxy, amino, and combinations thereof.

"TBE" represents 1,1,2,2-tetrabromo ethane.

"TFA" represents trifluoroacetic acid.

"THF" is tetrahydrofuran.

A "therapeutically effective amount" is an amount effective to reduce or lessen at least one symptom of the disease being treated or to reduce or delay onset of one or more clinical markers or symptoms of the disease.

"Thio" refers to the group —SZ$^1$Z$^2$ wherein each of Z$^1$ and Z$^2$ is independently selected from hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, and combinations thereof.

"TLC" is thin layer (SiO$_2$) chromatography.

The above term descriptions are provided solely to aid the reader, and should not be construed to have a scope less than that understood by a person of ordinary skill in the art or as limiting the scope of the appended claims.

The singular terms "a," "an," and "the" include plural referents unless context clearly indicates otherwise. Similarly, the word "or" is intended to include "and" unless the context clearly indicates otherwise. The word "comprises" indicates "includes." It is further to be understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting. All chemical compounds disclosed herein include both the (+) and (−) stereoisomers (as well as either the (+) or (−) stereoisomer), and any tautomers thereof.

An analog is a molecule that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in Remington: *The Science and Practice of Pharmacology*, 19$^{th}$ Edition (1995), chapter 28. A derivative is a biologically active molecule derived from the base structure.

Compounds are identified throughout this detailed description using reference numerals in bold, which correspond to the identification of the compounds in Tables 1 or 2, synthesis schemes 1 or 2, or the examples.

The presently described novel compounds having the structure of formula (I) include both an oxoquinoline ring structure and a diketo ring substituent. The compounds disclosed herein are diketo compounds in the sense that in formula (I) the Z substituent and/or at least one of R$_3$, R$_4$, R$_5$ and R$_6$ is a diketo group having the formula (II)

The compounds may contain geometric or optical isomers as well as tautomers. It should be recognized that the presently described diketo-acid/ester compounds can exist as tautomers in which the same compound can also be depicted as having a structure as shown in formula (III)

By naming and referring to a compound of formula (I) and tautomers thereof, it is understood that the tautomers of formulae (II) and (III) are intended.

According to certain examples, R$_7$ is independently selected from pyridyl, thienyl, naphthyl or phenyl, wherein the phenyl is unsubstituted or independently substituted on a carbon atom by at least one substituent selected from halogen, —CH$_3$, —OR$_2$, or —NO$_2$. In particular, R$_1$ is —H or a halogen-substituted arylalkyl.

In further examples, Z is particularly —C(O)CH$_2$C(O)C(O)OR$_2$ or —C(O)OR$_2$ wherein R$_2$ is —H, methyl or ethyl ("Et").

In select examples, R$_4$ and R$_5$ are each individually —H, -halogen, or —C(O)CH$_2$C(O)C(O)OR$_2$ wherein R$_2$ is —H, methyl or ethyl ("Et"). More particularly, if Z is —C(O)CH$_2$C(O)X then R$_4$ and R$_5$ are each individually —H or -halogen, and if Z is —C(O)OR$_2$ then R$_4$ is —C(O)CH$_2$C(O)C(O)OR$_2$ and R$_5$ is —H or -halogen.

In further examples, R$_3$ and R$_6$ are each individually —H.

In certain examples, at least one of R$_3$, R$_4$, R$_5$ and R$_6$ is a 5 or 6-membered heteroalicyclic ring containing 1 or 2 nitrogen heteroatoms.

In select examples, Z and R$_4$ are each —C(O)CH$_2$C(O)C(O)OR$_2$ wherein R$_2$ is —H, methyl or ethyl ("Et").

Specific examples of compounds disclosed herein are listed below in Tables 1, 2, 3 and 4. The compound identification numbers used in Tables 1-4 will be used throughout this specification.

TABLE 1

| Compound | $R_{11}$ | $R_{12}$ | $R_{14}$ | $R_{13}$ |
|---|---|---|---|---|
| RDS 1625 4a | H | H | H | 4-fluorophenylmethyl |
| RDS 1624 3a | H | H | Et | 4-fluorophenylmethyl |
| RDS 1787 4b | Cl | H | H | 4-fluorophenylmethyl |
| RDS 1755 3b | Cl | H | Et | 4-fluorophenylmethyl |
| RDS 1792 4c | H | Cl | H | 4-fluorophenylmethyl |
| RDS 1788 3c | H | Cl | Et | 4-fluorophenylmethyl |
| RDS 1680 6a | H | H | H | H |
| RDS 1675 5a | H | H | Et | H |
| RDS 1786 6b | Cl | H | H | H |
| RDS 1754 5b | Cl | H | Et | H |
| RDS 1794 6c | H | Cl | H | H |
| RDS 1793 5c | H | Cl | Et | H |
| RDS 1980 | H | H | Et | (4-phenylbutyl) |
| RDS 1981 | H | H | H | (4-phenylbutyl) |
| RDS 1974 | H | H | Et | (naphthalen-2-ylmethyl) |
| RDS 1975 | H | H | H | (naphthalen-2-ylmethyl) |
| RDS 2085 | H | H | Et | (pyridin-4-ylmethyl) |
| RDS 2086 | H | H | H | (pyridin-4-ylmethyl) |
| RDS 1999 | H | H | Et | (quinolin-2-ylmethyl) |
| RDS 2000 | H | H | H | (quinolin-2-ylmethyl) |
| RDS 2077 | F | H | Et | 4-fluorophenylmethyl |
| RDS 2078 | F | H | H | 4-fluorophenylmethyl |
| RDS 1755 | Cl | H | Et | 4-fluorophenylmethyl |
| RDS 1787 | Cl | H | H | 4-fluorophenylmethyl |
| RDS 2021 | H | F | Et | 4-fluorophenylmethyl |
| RDS 2022 | H | F | H | 4-fluorophenylmethyl |
| RDS 1788 | H | Cl | Et | 4-fluorophenylmethyl |
| RDS 1792 | H | Cl | H | 4-fluorophenylmethyl |
| RDS 2196 | H | 1-pyrrolidinyl | Et | 4-fluorophenylmethyl |
| RDS 2197 | H | 1-pyrrolidinyl | H | 4-fluorophenylmethyl |
| RDS 2225 | F | F | Et | 4-fluorophenylmethyl |
| RDS 2226 | F | F | H | 4-fluorophenylmethyl |
| RDS 2187 | Cl | Cl | Et | 4-fluorophenylmethyl |
| RDS 2188 | Cl | Cl | H | 4-fluorophenylmethyl |

TABLE 2

| Compound | $R_{15}$ | $R_{16}$ |
|---|---|---|
| RDS 1607 11 | HOOC—C=O | H |
| RDS 1606 10 | EtOOC—C=O | Et |

TABLE 3

| Compound | R | X |
|---|---|---|
| RDS 2080 | H | Et |
| RDS 2081 | H | H |

TABLE 3-continued

[Structure: quinolin-4-one with diketo substituents at 3- and 6-positions, XOOC and COOX groups, N-R substituent]

| Compound | R | X |
|---|---|---|
| RDS 1996 | 4-fluorobenzyl | Et |
| RDS 1997 | 4-fluorobenzyl | H |

TABLE 4

[Structure: quinolin-4-one with diketo substituent at 3-position, COOX group, N-benzyl with R substituent]

| Compound | R | X |
|---|---|---|
| RDS 1992 | H | Et |
| RDS 1993 | H | H |
| RDS 1989 | 2-F | Et |
| RDS 1990 | 2-F | H |
| RDS 1986 | 3-F | Et |
| RDS 1987 | 3-F | H |
| RDS 1624 | 4-F | Et |
| RDS 1625 | 4-F | H |
| RDS 2011 | 4-Cl | Et |
| RDS 2012 | 4-Cl | H |
| RDS 2173 | 4-OH | Et |
| RDS 2174 | 4-OH | H |
| RDS 2163 | 2-OCH$_3$ | Et |
| RDS 2164 | 2-OCH$_3$ | H |
| RDS 2160 | 3-OCH$_3$ | Et |
| RDS 2161 | 3-OCH$_3$ | H |
| RDS 2034 | 4-OCH$_3$ | Et |
| RDS 2035 | 4-OCH$_3$ | H |
| RDS 2017 | 4-NO$_2$ | Et |
| RDS 2018 | 4-NO$_2$ | H |
| RDS 1983 | 2,6-F$_2$ | Et |
| RDS 1984 | 2,6-F$_2$ | H |

Compound RDS 2107 has the structure of formula (I) wherein $R_3$, $R_4$ and $R_5$ are each H, $R_6$ is F, $R_1$ is 4-fluorophenylmethyl, and Z is —C(O)CH$_2$C(O)C(O)OEt. Compound RDS 2108 has the structure of formula (I) wherein $R_3$, $R_4$ and $R_5$ are each H, $R_6$ is F, $R_1$ is 4-fluorophenylmethyl, and Z is —C(O)CH$_2$C(O)C(O)OH. RDS 2111 has the structure of formula (I) wherein $R_3$, $R_4$ and $R_5$ are each H, $R_6$ is Cl, $R_1$ is 4-fluorophenylmethyl, and Z is —C(O)CH$_2$C(O)C(O)OEt. RDS 2112 has the structure of formula (I) wherein $R_3$, $R_4$ and $R_5$ are each H, $R_6$ is F, $R_1$ is 4-fluorophenylmethyl, and Z is —C(O)CH$_2$C(O)C(O)OH.

In the compounds of Table 1 the diketo substituent is located at a 3-position on the oxoquinoline ring relative to the 1-position nitrogen heteroatom. The presence of the oxo group at the 4-position on the oxoquinoline ring permits the synthesis of compounds having a diketo substituent at the 3-position and a substituent (e.g., a benzyl group) at the nitrogen atom. In the compounds of Table 2 the diketo substituent is located on the ring that does not contain the nitrogen heteroatom.

In general, 3-acetyl-quinoline-4-ones were alkylated (at 60-120° C., 0.5-24 hrs.) in the 1-position with an appropriate alkyl halide (e.g., 4-fluorobenzylbromide, 4-F-benzylchloride, 4-F-benzyliodide) in alkaline medium (e.g., K$_2$CO$_3$, Na$_2$CO$_3$, NaH, NaNH$_2$) to obtain the N-substituted derivatives. The alkylation can occur in the presence of DMSO, THF, dioxane or DMF. The N-substituted derivatives were condensed (at room temp.–60° C., 0.5-48 hrs.) with a dialkyl oxalate (e.g., diethyl oxalate) in presence of an alkali compound (e.g., sodium ethoxide, alkylONa, NaH, NaNH$_2$) to give quinolin-3-yl-diketo esters. The quinolin-3-yl-diketo esters could then be hydrolyzed (at room temp.–60° C., 0.5-48 hrs.) to provide the corresponding acids in the presence of a suitable medium such as, for example, THF/H$_2$O, CH$_3$OH/H$_2$O or C$_2$H$_5$OH/H$_2$O. Illustrative hydrolysis reagents include KOH, Ca(OH)$_2$ and Ba(OH)$_2$.

Similarly, quinolin-4-ones having a diketo substituent in the 6-position were obtained as follows: 6-acetylquinolin-4-one-3-carboxylic esters underwent N-alkylation with an alkyl halide in the presence of anhydrous K$_2$CO$_3$ to provide the 1-substituted derivatives, which were condensated with diethyl oxalate, using sodium ethoxide as a catalyst, to obtain diketoesters. The diketoesters could then be easily hydrolyzed to provide the corresponding dicarboxylic acids. The reaction scheme for the 6-position diketo compounds can use the same reagent and reaction conditions as for the 3-position diketo compounds.

The presently described compounds, and pharmaceutically acceptable salts thereof, are useful for treating humans or animals suffering from a condition characterized by a replication or integration of a retrovirus and for helping to prevent or delay the onset of such a condition. For example, the compounds are useful for treating infection by HIV, AIDS, or AIDS related complex (ARC). When treating or preventing these diseases, the compounds can either be used individually or in combination, as is best for the patient.

More particularly, the compounds and pharmaceutical compositions can be used in the treatment of a variety of retroviral diseases caused by infection with retroviruses that require integrase activity for infection and viral replication. Examples of such diseases include HIV-1, HIV-2, simian immunodeficiency virus (SIV), feline immunodeficiency virus (FIV), HTLV-1, HTLV-2, spumavirus (human foamy virus) and feline infectious leukemia.

The compounds and pharmaceutical compositions are especially useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds are useful in treating infection by HIV after suspected past exposure to HIV by e.g., blood transfusion, exchange of body fluids, bites, accidental needle stick, or exposure to patient blood during surgery.

As used herein, the term "treating" means that the compounds can be used in humans with at least a tentative diagnosis of disease. The compounds will delay or slow the progression of the disease thereby giving the individual a more useful life span.

The term "preventing" means that the compounds are useful when administered to a patient who has not been diagnosed as possibly having the disease at the time of administration, but who would normally be expected to develop the disease or be at increased risk for the disease. The compounds will slow the development of disease symptoms, delay the onset of the disease, or prevent the individual from developing the disease at all.

In treating or preventing the above diseases, the compounds are administered in a therapeutically effective amount. The therapeutically effective amount will vary depending on the particular compound used and the route of administration, as is well known.

In treating a patient displaying any of the diagnosed above conditions a physician may administer a compound immediately and continue administration indefinitely, as needed. Upon HIV infection or exposure, even though the patient does not have symptoms of disease, administration of the compounds may be started before symptoms appear, and treatment may be continued indefinitely to prevent or delay the onset of disease.

The compounds are useful in the preparation and execution of screening assays for antiviral compounds. For example, the compounds are useful for isolating enzyme mutants, which are excellent screening tools for more powerful antiviral compounds. Furthermore, the compounds are useful in establishing or determining the binding site of other antivirals to HIV integrase, e.g., by competitive inhibition. Also included are methods of screening for an anti-HIV integrase drug, by providing an assay of HIV integrase inhibition, and using the assay to screen for drugs that are analogs or derivatives of any of the disclosed compounds, and which inhibit HIV integrase. In particular examples, the assay detects a diketo oxoquinoline compound that inhibits HIV-1 integrase.

The treatment disclosed herein involves administering to a patient in need of such treatment a pharmaceutical composition that includes a pharmaceutically acceptable carrier and a therapeutically-effective amount of the presently described compound. The compounds may be administered orally, parenterally (including subcutaneous injections (SQ and depo SQ), intravenous (IV), intramuscular (IM and depo-IM), intrasternal injection or infusion techniques), sublingually, intranasally (inhalation), intrathecally, topically, opthalmically or rectally, in dosage unit formulations containing conventional non-toxic pharmaceutically-acceptable carriers, adjuvants and vehicles. Dosage forms known to those of skill in the art are suitable for delivery of the compounds.

The terms "administration of" and or "administering a" compound should be understood to mean providing a compound, a prodrug of a compound, or a pharmaceutical composition as described herein.

Pharmaceutical compositions are provided that contain therapeutically effective amounts of the presently described compounds. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

About 1 to 500 mg of a compound or mixture of compounds or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds are mixed or combined with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The compounds may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of the compound is effective for delivery of an amount upon administration that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only.

Pharmaceutical compositions may be in a form acceptable for oral (suspensions or tablets for example), parenteral (including subcutaneous injections (SQ and depo SQ), intravenous (IV), intramuscular (IM and depo-IM), intrasternal injection or infusion techniques), sublingual, intranasal (nasal spray for example), intrathecal, topical (ointment), rectal (suppository), or through implant administration, for example.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily.

The oral dosage forms are administered to the patient 1, 2, 3, or 4 times daily. It is preferred that the compounds be administered either three or fewer times, more preferably once or twice daily. It is preferred that whatever oral dosage form is used, that it be designed so as to protect the compounds from the acidic environment of the stomach. Enteric coated tablets are well known to those skilled in the art. In addition, capsules filled with small spheres, each coated to protect from the acidic stomach, are also well known to those skilled in the art.

When administered orally, an administered amount therapeutically effective to inhibit retroviral integrase activity, to inhibit retroviral integrase mediated strand transfer, to inhibit retroviral mediated incorporation of a donor DNA into a receiving DNA, to inhibit HIV replication, to inhibit, prevent, or treat HIV infection, to treat or prevent AIDS is from about 0.1 mg/day to about 1,000 mg/day. In certain examples, the oral dosage is from about 1 mg/day to about 100 mg/day. In yet other examples, the oral dosage is from about 5 mg/day to about 50 mg/day. It is understood that while a patient may be started at one dose, that dose may be varied over time as the patient's condition changes.

The compounds can be administered orally to humans in a dosage range of 1 to 1000 mg/kg body weight in single or divided doses. One illustrative dosage range is 0.1 to 200 mg/kg body weight orally in single or divided doses. Another illustrative dosage range is 0.5 to 100 mg/kg body weight orally in single or divided doses. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.5 to about 100 mg/day, more particularly from about 5 to about 50 mg daily should be delivered. When a depot formulation is used for injection once a month or once every two weeks, the dose may be about 0.5 mg/day to about 50 mg/day, or a monthly dose of from about 15 mg to about 1,500 mg.

The compounds can be administered sublingually. When given sublingually, the compounds should be given one to four times daily in the amounts described above for IM administration.

The compounds can be administered intranasally. When given by this route, the appropriate dosage forms are a nasal spray or dry powder. The dosage of the compounds for intranasal administration is the amount described above for IM administration.

When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used. The compounds can be administered rectally by suppository. When administered by suppository, an illustrative therapeutically effective amount may range from about 0.5 mg to about 500 mg.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds can be administered by implants. When administering a compound by implant, the therapeutically effective amount is the amount described above for depot administration.

The compounds may be used in the same manner, by the same routes of administration, using the same pharmaceutical dosage forms, and at the same dosing schedule as described above, for preventing disease or treating patients with HIV infection, AIDS, or ARC.

The presently described compounds may also be used in combination with a therapeutically effective amount of an AIDS treatment agent such as nucleoside analog reverse transcriptase inhibitors, non-nucleoside reverse transcriptase inhibitors, protease inhibitors, other antivirals, immunomodulators, anti-infectives, other antibiotics, or other medicines useful against HIV infection, AIDS, or ARC.

Suitable antivirals of all categories include Amprenivir, Abacavir, Acyclovir, Adefovir dipivoxil, Alpha Interferon, Retrovir, Ansamycin, beta-fluoro-ddA, Cidofovir, Curdlan sulfate, Cytovene, Ganciclovir, Delaviridine, Dideoxycytidine, Dideoxyinosine, Efavirenz, Famciclovir, Hypericin, Interferon Beta, Interferon alfa-n3, Indinavir, Lamivudine, Lobucavir, Nelfinavir, Nevirapine, Novapren, Phosphonoformate, Probucol, Ritonavir, Saquinavir, Didehydrodeoxythymidine, Valaciclovir, Virazole, Ribavirin, Zalcitabine, and Zidovudine (AZT).

Suitable immunomodulators include Bropirimine, Acemannan, interferons such as gamma interferon and alpha interferon, tumor necrosis factor, granulocyte macrophage colony stimulating factor, interleukin-2, recombinant or soluble CD4.

Suitable anti-infectives include Clindamycin, Primaquine, Fluconazole, Pastille, Nystatin Pastille, Ornidyl, Eflornithine, Pentamidine, Isethionate, Trimethoprim, Trimethoprim/sulfa, Piritrexim, Pentamidine, Spiramycin, Trimetrexate.

Examples of combination therapy are simultaneous or alternating treatments with a presently described compound and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Suitable HIV protease inhibitors include indinavir, nelfinavir, ritonavir, and saquinavir. Suitable non-nucleoside inhibitors of HIV reverse transcriptase include nevirapine and efavirenz.

In such combinations the compounds and other active agents may be administered separately or in conjunction. In addition, the administration of one element may be prior to, concurrent to, or subsequent to the administration of other agent(s).

It should be apparent to one skilled in the art that the exact dosage and frequency of administration will depend on the particular compounds administered, the particular condition being treated, the severity of the condition being treated, the age, weight, general physical condition of the particular patient, and other medication the individual may be taking as is well known to administering physicians who are skilled in therapy of retroviral infections, diseases, and associated disorders.

Various assays for measuring activities of retroviral integrase are known. For example, assays for the strand transfer activity of integrase can be conducted according to Wolfe et al., *J. Virol.* 70:1424, 1996, and Farnet et al., *Cell* 88:483, 1997, for recombinant integrase and preintegration complexes. In addition, assays for the inhibition of acute HIV infection of T-lymphoid cells can be conducted according to Vacca et al., *Proc. Natl. Acad. Sci. USA* 91:4906, 1994.

Methods of determining inhibition of retroviral integrase in vitro and in vivo can also be determined, for example, in accordance with procedures given in the examples included herein. See Mazumder et al., "Retroviral Integrase: A Novel Target in Antiviral Development; Basic In Vitro Assays with the Purified Enzyme," in: *Antiviral Methods and Protocols*, D. Kinchington and R. Schinazi (eds.), pp. 327-335. Totowa, N.J.: The Humana Press, Inc., 1999, and also Marchand et al., "In vitro human immunodeficiency virus type 1 integrase assays," *Methods Enzymol.* 340:624-633, 2001.

EXAMPLE 1

General Preparation of 4-(1,4-dihydro-4-oxoquinolin-3-yl)-2,4-dioxobutanoic Acid Ethyl Esters and their Corresponding Acids Scheme 1 below shows an illustrative chemical pathway for the synthesis of the compounds described above in Table 1. The 3-acetyl-4(1H)-quinolinones 1 that were used as starting materials were prepared according to Sinsky et al., *Journal of Heterocyclic Chemistry* 21:759-76, 1984, by reacting the desired anilines with 3-butyn-2-one, followed by cyclization with methanolic sodium methoxide. According to synthesis route (i), reaction (i.e., alkylation) of compound 1 with 4-fluorophenylmethylbromide gave the N-arylmethylquinolinones 2 that were then condensed with diethyl oxalate in the presence of sodium ethoxide to provide 4-[1,4-dihydro-(4-fluorophenyl)methyl-4-oxoquinolin-3-yl]-2,4-dioxobutanoic acid ethyl esters 3. Alkaline hydrolysis of compound 3 led to the corresponding 4-[1,4-dihydro-(4-fluorophenyl)methyl-4-oxoquinolin-3-yl]-2,4-dioxobutanoic acids 4. According to synthesis route (ii), coupling of 4-quinolinones 1 with diethyl oxalate in the presence of the sodium ethoxide, followed by alkaline hydrolysis of the resulting ethyl esters 5 gave acids 6. Finally, the 3-acetyl-4(1H)-quinolinones 1 were oxidized with $SeO_2$ in pyridine to achieve the corresponding α-keto acids 7.

-continued $R_1$ = H, Cl
$R_2$ = H, Cl

[a]Reagents: (i) 4-fluorobenzylbromide, $K_2CO_3$, DMF, 100° C.; (ii) diethyl oxalate, NaOEt, 25° C.; (iii) 1N NaOH, 25° C.; (iv) $SeO_2$, pyridine, 100° C.

EXAMPLE 2

General Preparation of RDS 1606 (10) 4-[3-carboxyethyl-1,4-dihydro-1-(4-fluorophenyl)methyl-4-oxoquinolin-6-yl]-2,4-dioxobutanoic Acid, Ethyl Ester and RDS 1607 (11) 4-[3-carboxyethyl-1,4-dihydro-1-(4-fluorophenyl)methyl-4-oxoquinolin-6-yl]-2,4-dioxobutanoic Acid Scheme 2 below shows an illustrative chemical pathway for the synthesis of the compounds described above in Table 2. The 1,4-dihydro-6-acetyl-4-oxoquinoline-3-carboxylic acid ethyl ester 8 was prepared according to Koga et al., *Journal of Medicinal Chemistry* 23:1358-1363, 1980, by reacting the appropriate aniline with diethyl ethoxymethylenemalonate followed by thermal cyclization of the malonate derivative obtained. Alkylation of compound 8 with 4-fluorophenylmethylbromide in alkaline medium led to derivative 9 that was condensed with diethyl oxalate in presence of the sodium ethoxide to afford 4-[3-carboxyethyl-1,4-dihydro-1-(4-fluorophenyl)methyl-4-oxoquinolin-6-yl]-2,4-dioxobutanoic acid, ethyl ester 10 (RDS 1606). Alkaline hydrolysis of the latter compound to provide 4-[3-carboxyethyl-1,4-dihydro-1-(4-fluorophenyl)methyl-4-oxoquinolin-6-yl]-2,4-dioxobutanoic acid 11 (RDS 1607) was carried out with aqueous 1N sodium hydroxide at room temperature, while hydrolysis of the quinolinecarboxylate ester 9 to afford corresponding acid 12 required 20% aqueous sodium hydroxide (Scheme 2).

Scheme 2[b]

[b]Reagents: (i) 4-fluorobenzylbromide, $K_2CO_3$, DMF, 100° C.;
(ii) diethyl oxalate, NaOEt, 25° C.;
(iii) 1N NaOH, 25° C.; (iv) 20% aqueous NaOH, EtOH, 25° C.

Another Synthesis Scheme is Depicted Below:

Scheme[a]

$R_1$ = H, Cl, F
$R_2$ = H, Cl, F
$R_3$ = H, Cl, F

3 X = Et
4 X = H

[a]Reagents: (i) Arylalkylhalide, $K_2CO_3$, DMF, 100° C.; (ii) diethyl oxalate, NaOEt, 25° C.; (iii) 1N NaOH, 25° C.; (iv) Pyrrolidine, $Et_3N$, DMF, MW, 100 Watt, 153° C.

EXAMPLE 3

Synthesis and Analytical Results of Specific Compounds 1,4-Dihydro-3-acetyl-4-oxoquinoline (1a). Compound 1a was obtained as a white solid according to Sinsky et al., supra; mp 242-244° C. (acetone). Compounds 1b ($R_1$=Cl, $R_2$=H) and 1c ($R_1$=H, $R_2$=Cl) were prepared by this method starting from appropriate anilines. Compound 1b: 29% yield; mp>300° C. (ethanol); compound 1c: 96% yield; mp>300° C. (ethanol).

1-(4-fluorophenyl)methyl-1,4-dihydro-3-acetyl-4-oxoquinoline (2a). A solution of 3-acetyl-4(1H)-quinolinone (1a) (0.8 g, 45 mmol) in dry DMF (40 mL) was treated with anhydrous $K_2CO_3$ (0.86 g, 62 mmol) and 4-fluorophenylmethylbromide (2.46 g, 13 mmol) and the resulting suspension was stirred for 1.5 hours at 100° C. After cooling, water was added (100 mL) and the precipitate that formed was filtered, washed with water, light petroleum ether in turn and then dried under IR lamp to provided compound 2a (0.86 g, 65%); mp 213-214° C. (toluene). Analogs 2b ($R_1$=$C_1$, $R_2$=H) and 2c ($R_1$=H, $R_2$=Cl) were similarly prepared by this method. Compound 2b: 92% yield; mp 214-216° C. (toluene/cyclohexane); compound 2c: 73% yield; mp 185-187° C. (toluene/cyclohexane).

4-[1-(4-fluorophenyl)methyl-1,4-dihydro-4-oxoquinolin-3-yl]-2,4-dioxobutanoic acid ethyl ester (RDS 1624, 3a). Sodium ethoxide (0.39 g, 5.5 mmol) was added into a well stirred mixture of compound 2a (0.79 g, 2.7 mmol) and diethyl oxalate (0.79 g, 5.4 mmol) in anhydrous THF (2.7 mL) under nitrogen atmosphere. The mixture was stirred at room temperature for 1 hour and 45 minutes, then was poured into hexane (50 mL). The collected precipitate was vigorously stirred for 30 minutes in 1N HCl (50 mL). The yellow solid that formed was filtered, washed with water and dried under IR lamp to afford 3a (0.88 g, 82%); mp 175-177° C. (ethanol). Compounds 3b and 3c (Table 1) were prepared by this method starting from the corresponding quinolines 2b and 2c, respectively. Compound RDS 1755 (3b): 34% yield; mp 131-133° C. (washed with cyclohexane). Compound RDS 1788 (3c): 76% yield; mp 173-175° C. (washed with isopropanol). The following spectroscopy data was obtained for these compounds:

RDS 1624 (3a)

IR 3400 (OH), 1721 (CO ester), 1661 and 1607 (CO ketone), 1635 (CO quinolinone) $cm^{-1}$. $^1$H NMR ($CDCl_3$) δ 1.44 (t, 3H, $CH_3$), 4.42 (q, 2H, $CH_2CH_3$), 5.48 (s, 2H, $CH_2$), 7.06-7.26 (m, 4H, benzene H), 7.39 (m, 1H, quinolinone $C_6$—H), 7.51 (m, 1H, quinolinone $C_7$—H), 7.63 (m, 1H, quinolinone $C_8$—H), 8.16 (s, 1H, butenoate $C_3$—H), 8.56 (m, 1H, $C_5$—H quinolinone), 8.77 (s, 1H, $C_2$—H quinolinone), 15.50 (bs, 1H, OH).

RDS 1755 (3b)

IR 3400 (OH), 1722 (CO ester), 1700 and 1628 (CO ketone) $cm^{-1}$. $^1$H NMR (DMSO-$d_6$) δ 1.33 (t, 3H, $CH_3$), 4.33 (q, 2H, $CH_2CH_3$), 5.71 (s, 2H, $CH_2$), 7.14-7.34 (m, 4H, benzene H), 7.71-7.77 (m, 2H, quinolinone $C_7$—H and $C_8$—H), 7.91 (s, 1H, butenoate $C_3$—H), 8.25 (m, 1H, quinolinone $C_5$—H), 9.09 (s, 1H, quinolinone $C_2$—H), 12.70 (bs, 1H, OH).

RDS 1788 (3c)

IR 3300 (OH), 1727 (CO ester), 1647 (CO ketone) $cm^{-1}$. $^1$H NMR (DMSO-$d_6$) δ 1.30 (t, 3H, $CH_3$), 4.32 (q, 2H, $CH_2CH_3$), 5.76 (s, 2H, $CH_2$), 7.16-7.25 (m, 2H, benzene H), 7.36-7.38 (m, 2H, benzene H), 7.54 (m, 1H, quinolinone $C_6$—H), 7.88 (m, 1H, quinolinone $C_8$—H), 7.96 (s, 1H, butenoate $C_3$—H), 8.29 (m, 1H, quinolinone $C_5$—H), 9.08 (s, 1H, quinolinone $C_2$—H), 12.70 (bs, 1H, OH).

4-[1-(4-fluorophenyl)methyl-1,4-dihydro-4-oxoquinolin-3-yl]-2,4-dioxobutanoic acid (RDS 1625, 4a). A mixture of 1N NaOH (6.5 mL) and compound 3a (0.5 g, 1.3 mmol) in THF/methanol 1:1 (12 mL) was stirred at room temperature for 18 hours and then poured onto crushed ice. The aqueous layer was separated and treated with 1N HCl until reaching pH 3 and the yellow solid that formed was collected by filtration then washed with hot dry ethanol and light petroleum ether to give compound 4a (0.24 g, 50%); mp 207-209° C. (washed with hot anhydrous ethanol). Compounds 4b and 4c (Table 1) were prepared by this method starting from the corresponding esters 3b and 3c, respectively. Compound RDS 1787 (4b): 71% yield; mp 194-197° C. (DMF/water). Compound RDS 1792 (4c): 64% yield; mp 188-190° C. (washed with isopropanol). The following spectroscopy data was obtained for these compounds:

RDS 1625 (4a)

IR 3400 (OH), 1732 (CO acid), 1619 (CO ketone) cm$^{-1}$. $^1$H NMR (CDCl$_3$) δ 5.79 (s, 2H, CH$_2$), 7.22-7.38 (m, 4H, benzene H), 7.53 (m, 1H, quinolinone $C_6$—H), 7.76 (m, 2H, quinolinone $C_7$—H and $C_8$—H), 8.01 (s, 1H, butenoate $C_3$—H), 8.34 (m, 1H, quinolinone $C_5$—H), 9.16 (s, 1H, quinolinone $C_2$—H), 15.50 (bs, 2H, OH).

RDS 1787 (4b)

IR 3385 (OH), 1710 (CO acid), 1663 and 1622 (CO ketone) cm$^{-1}$. $^1$H NMR (DMSO-d$_6$) δ 5.72 (s, 2H, CH$_2$), 7.18-7.32 (m, 4H, benzene H), 7.75-7.85 (m, 2H, quinolinone $C_7$—H and $C_8$—H), 8.22 (m, 1H, $C_5$—H quinolinone), 7.90 (s, 1H, butenoate $C_3$—H), 9.08 (s, 1H, quinolinone $C_2$—H), 13.00 (bs, 2H, OH).

RDS 1792 (4c)

IR 3400 (OH), 1734 (CO acid), 1646 (CO ketone) cm$^{-1}$. $^1$H NMR (DMSO-d$_6$) δ 5.75 (s, 2H, CH$_2$), 7.21-7.36 (m, 4H, benzene H), 7.55 (m, 1H, quinolinone $C_6$—H), 7.83-7.85 (m, 2H, quinolinone $C_8$—H and butenoate $C_3$—H), 8.30 (m, 1H, quinolinone $C_5$—H), 9.07 (s, 1H, quinolinone $C_2$—H), 13.00 (bs, 2H, OH).

4-(1,4-dihydro-4-oxoquinolin-3-yl)-2,4-dioxobutanoic acid ethyl ester (RDS 1675, 5a). A mixture of 3-acetyl-4-oxoquinoline (1a) (0.50 g, 2.67 mmol), diethyl oxalate (0.78 g, 5.34 mmol) and sodium ethoxide (0.48 g, 6.8 mmol) in anhydrous THF (2.67 mL) was stirred at room temperature for 24 hours under nitrogen atmosphere. Then the solution was poured into hexane (50 mL) and the precipitate that formed was collected by filtration and vigorously stirred for 30 minutes in 1N HCl (50 mL). The yellow solid that was obtained was filtered, washed with water and dried under IR lamp. Recrystallization provided pure compound 5a (0.24 g, 43%); mp 235-237° C. (DMF/water). Compounds 5b and 5c (Table 1) were prepared by this method starting from the corresponding quinolines 1b and 1c, respectively. Compound RDS 1754 (5b): 57% yield; mp 209-211° C. (ethanol). Compound RDS 1793 (5c): 77% yield; mp 187-189° C. (washed with isopropanol). The following spectroscopy data was obtained for these compounds:

RDS 1675 (5a)

IR 3200 (NH and OH), 1710 (CO ester), 1620 and 1600 (CO ketone) cm$^{-1}$. $^1$H NMR (DMSO-d$_6$) δ 1.35 (t, 3H, CH$_3$), 4.32 (q, 2H, CH$_2$), 7.47-7.55 (m, 1H, quinolinone $C_6$—H), 7.67-7.83 (m, 2H, quinolinone $C_7$—H and $C_2$—H), 8.03 (s, 1H, butenoate $C_3$—H), 8.24-8.27 (m, 1H, $C_5$—H quinolinone), 8.79 (s, 1H, quinolinone $C_2$—H), 12.90 (bs, 1H, NH), 15.75 (bs, 1H, OH).

RDS 1754 (5b)

IR 3300 (NH and OH), 1734 (CO ester), 1684 (CO ketone) cm$^{-1}$. $^1$H NMR (DMSO-d$_6$) δ 1.31 (t, 3H, CH$_3$), 4.25 (q, 2H, CH$_2$), 7.40-7.80 (m, 2H, quinolinone $C_7$—H and $C_8$—H), 8.00 (s, 1H, butenoate $C_3$—H), 8.20 (m, 1H, quinolinone $C_5$—H), 8.50 (s, 1H, quinolinone $C_2$—H), 12.75 (bs, 2H, NH and OH).

RDS 1793 (5c)

IR 3200, 3064 (NH and OH), 1726 (CO ester), 1700 and 1624 (CO ketone) cm$^{-1}$. $^1$H NMR (DMSO-d$_6$) δ 1.30 (t, 3H, CH$_3$), 4.30 (q, 2H, CH$_2$), 7.47 (m, 1H, quinolinone $C_6$—H), 7.68 (s, 1H, quinolinone $C_8$—H), 7.94 (s 1H, butenoate $C_3$—H), 8.18 (m, 1H, quinolinone $C_5$—H), 8.77 (s, 1H, quinolinone $C_2$—H), 13.00 (bs, 1H, NH and OH).

4-(1,4-dihydro-4-oxoquinolin-3-yl)-2,4-dioxobutanoic acid (RDS 1680, 6a). To a solution of compound 5a (0.19 g, 6.6 mmol) in THF/methanol 1:1 (6 mL) was added 1N NaOH (3.3 mL). The mixture reaction was stirred at room temperature for 24 hours, then more 1N NaOH (1 mL) was added. After 1 hour and 50 minutes the mixture was poured onto crushed ice and extracted with ethyl acetate (5×10 mL). The aqueous layer was treated with 1N HCl until pH 3. The resulting yellow solid was collected by filtration then washed with water, dry ethanol and light petroleum ether in turn to give compound 6a (0.08 g, 47%); mp>290° C. (washed with dry ethanol). Compounds 6b, and 6c (Table 1) were prepared by this method from corresponding esters 5b and 5c, respectively. Compound RDS 1786 (6b): 50% yield; mp 220 (dec)° C. (toluene/cyclohexane); Compound RDS 1794 (6c): 52% yield; mp 200 (dec)° C. (washed with isopropanol). The following spectroscopy data was obtained for these compounds:

RDS 1680 (6a)

IR 3400, 3214 (NH and OH), 1715 (CO acid), 1622 (CO ketone) cm$^{-1}$. $^1$H NMR (DMSO-d$_6$) δ 7.52 (m, 1H, quinolinone $C_6$—H), 7.62 (m, 2H, quinolinone $C_7$—H and $C_8$—H), 7.99 (m, 1H, butenoate $C_3$—H), 8.26 (m, 1H, quinolinone $C_5$—H), 8.79 (s, 1H, quinolinone $C_2$—H), 13.00 (bs, 3H, NH and OH).

RDS 1786 (6b)

IR 3400, 3200 (NH and OH), 1718 (CO acid), 1640 and 1611 (CO ketone) cm$^{-1}$. $^1$H NMR (DMSO-d$_6$) δ 7.72-7.75 (m, 2H, quinolinone $C_7$—H and $C_8$—H), 8.13 (s, 1H, butenoate $C_3$—H), 8.53 (m, 1H, quinolinone $C_5$—H), 8.80 (s, 1H, quinolinone $C_2$—H), 13.00 (bs, 3H, NH and OH).

RDS 1794 (6c)

IR 3400, 3200 (NH and OH), 1740 (CO acid), 1640 and 1616 (CO ketone) cm$^{-1}$. $^1$H NMR (DMSO-d$_6$) δ 7.47 (m, 1H, quinolinone $C_6$—H) 7.69 (m, 1H, quinolinone $C_9$—H), 7.92 (s, 1H, butenoate $C_3$—H), 8.21 (m, 1H, quinolinone $C_5$—H), 8.88 (s, 1H, quinolinone $C_2$—H), 12.75 (bs, 3H, NH and OH).

Compound RDS 1771 (7). A solution of compound 2a (0.2 g, 6.7 mmol) in dry pyridine (3 mL) was treated with SeO$_2$ (0.12 g, 10.7 mmol) and heated at 100° C. for 3.5 hours. After cooling the suspension was filtered and the filtrate was dissolved in ethyl acetate. The organic layer washed with 1N HCl and brine and then the solvent was removed under reduced pressure to provide pure compound 7 (0.15 g, 69%); mp 223-225° C. (ethanol).

1-(4-fluorophenyl)methyl-1,4-dihydro-6-acetyl-4-oxoquinoline-3-carboxylic acid ethyl ester (compound 9). A suspension of ester compound 8 (0.6 g, 2.3 mmol) 4-fluorophenylmethyl chloride (0.97 g, 6.8 mmol) and anhydrous $K_2CO_3$ (0.44 g, 6.8 mmol) in dry DMF (20 mL) was stirred for 18 hours at 100° C. After this time the mixture was poured into water (100 mL) and the solid that precipitated was filtered, washed with water, ethanol and light petroleum ether, in turn, and finally dried under IR lamp to give compound 9 (0.75 g, 95%); mp 207-209° C. (washed with dry ethanol).

1-(4-fluorophenyl)methyl-1,4-dihydro-6-acetyl-4-oxo-quinoline-3-carboxylic acid (compound 12). A solution of compound 9 (0.46 g, 1.3 mmol) and 20% aqueous NaOH (4.3 mL) in ethanol (3 mL) was stirred for 18 hours at room temperature, then was poured into water (100 mL) and treated with 1N HCl until pH 3. The precipitate was filtered, washed with dry ethanol and light petroleum ether to give compound 12 (0.36 g, 88%); mp 206-208° C. (washed with dry ethanol).

Compound RDS 1606 (10). To a solution of compound 9 (1 g, 2.9 mmol) and diethyl oxalate (0.84 g, 5.8 mmol) in anhydrous THF (2.9 mL) was added NaOEt (0.13 g, 5.7 mmol) under $N_2$ protection. After 1 hour and 30 minutes at room temperature the mixture was poured into hexane (50 mL). The precipitate was removed by filtration and then was vigously stirred for 30 minutes in 1N HCl (50 mL). The yellow solid was filtered, washed with water and dried under IR lamp to yield compound 10 (0.71 g, 52%); mp 177-180° C. (DMF/water). The following spectroscopy data was obtained: IR 3300 (OH), 1720 (CO ester), 1670 (CO ketone) $cm^{-1}$. $^1$H NMR (DMSO-$d_6$) δ 1.32 (t, 6H, $CH_3$), 4.29 (q, 4H, $CH_2CH_3$), 5.72 (s, 2H, $CH_2$), 7.16-7.35 (m, 5H, benzene H and butenoate $C_3$—H), 7.79 (m, 1H, quinolinone $C_8$—H), 8.28 (m, 1H, quinolinone $C_7$—H), 8.82 (m, 1H, quinolinone $C_5$—H), 8.98 (s, 1H, quinolinone $C_2$—H), 14.00 (bs, 1H, OH).

Compound RDS 1607 (11). To a solution of compound 10 (0.66 g, 14 mmol) in THF/methanol 1:1 (13 mL) was added 1N NaOH (14 mL). The mixture reaction was stirred at room temperature for 23 hours, and then poured onto crushed ice. The aqueous layer was treated with 1N HCl until pH 3. The resulting yellow solid was collected by filtration, washed with chloroform and light petroleum ether and then dried under IR lamp to give compound 11 (0.43 g, 75%); mp 184-187° C. (DMF/water). The following spectroscopy data was obtained: IR 3400 (OH), 1710 (CO acid) $cm^{-1}$. $^1$H NMR (DMSO-$d_6$) δ 5.91 (s, 2H, $CH_2$), 6.99 (s, 1H, $C_3$—H butenoate), 7.21-7.25 (m, 2H, benzene H), 7.30-7.40 (m, 2H, benzene H), 8.00 (m, 1H, quinolinone $C_8$—H), 8.30-8.39 (m, 1H, quinolinone $C_7$—H), 8.89 (m, 1H, quinolinone $C_8$—H), 9.34 (s, 1H, quinolinone $C_2$—H), 14.70 (bs, 2H, OH).

Spectroscopy data for additional compounds is set forth below:

Quinolinyl 2,4-Dioxobutanoic Acid Ethyl Esters 4-(1-Phenylmethyl-1,4-dihydro-4-oxoquinolin-3-yl)-2,4-dioxobutanoic acid ethyl ester (RDS 1992). 99% yield; mp 141-142° C. (benzene). IR 1740 (CO ester), 1648 and 1629 (CO ketone) $cm^{-1}$. $^1$H NMR (DMSO-$d_6$) δ 1.30 (t, 3H, $CH_3$), 4.30 (q, 2H, $CH_2CH_3$), 5.77 (s, 2H, $CH_2$), 7.23-7.36 (m, 5H, benzene-H), 7.45-7.52 (m, 1H, quinolinone $C_6$—H), 7.69-7.74 (m, 2H, quinolinone $C_7$—H and $C_8$—H), 8.02 (s, 1H, butenoate $C_3$—H), 8.31-8.33 (m, 1H, quinolinone $C_5$—H), 9.12 (s, 1H, quinolinone $C_2$—H), 14.75 (bs, 1H, OH).

4-[1-(2-Fluorophenyl)methyl-1,4-dihydro-4-oxoquinolin-3-yl]-2,4-dioxobutanoic acid ethyl ester (RDS 1989). 92% yield; mp 152-153° C. (toluene). IR 1744 (CO ester), 1652 and 1612 (CO ketone) $cm^{-1}$. $^1$H NMR (DMSO-$d_6$) δ 1.29 (t, 3H, $CH_3$), 4.30 (q, 2H, $CH_2CH_3$), 5.81 (s, 2H, $CH_2$), 7.12-7.28 (m, 3H, benzene H), 7.34-7.52 (m, 2H, quinolinone $C_6$—H and benzene H), 7.68-7.76 (m, 2H, quinolinone $C_7$—H and $C_8$—H), 7.99 (s, 1H, butenoate $C_3$—H), 8.31-8.33 (m, 1H, quinolinone $C_5$—H), 9.09 (s, 1H, quinolinone $C_2$—H), 15.75 (bs, 1H, OH).

4-[1-(3-Fluorophenyl)methyl-1,4-dihydro-4-oxoquinolin-3-yl]-2,4-dioxobutanoic acid ethyl ester (RDS 1986). 94% yield; mp 174-175° C. (methanol). IR 1740 (CO ester), 1650 and 1613 (CO ketone) $cm^{-1}$. $^1$H NMR (DMSO-$d_6$) δ 1.29 (t, 3H, $CH_3$), 4.29 (q, 2H, $CH_2CH_3$), 5.78 (s, 2H, $CH_2$), 7.07-7.21 (m, 3H, benzene H), 7.35-7.51 (m, 2H, quinolinone $C_6$—H and benzene H), 7.66-7.74 (m, 2H, quinolinone $C_7$—H and $C_8$—H), 8.01 (s, 1H, butenoate $C_3$—H), 8.31-8.33 (m, 1H, quinolinone $C_5$—H), 9.12 (s, 1H, quinolinone $C_2$—H), 16.00 (bs, 1H, OH).

4-[1-(4-Chlorophenyl)methyl-1,4-dihydro-4-oxoquinolin-3-yl]-2,4-dioxobutanoic acid ethyl ester (RDS 2011). 91% yield; mp 174-176° C. (toluene). IR 1723 (CO ester), 1643 and 1611 (CO ketone) $cm^1$. $^1$H NMR (DMSO-$d_6$) δ 1.30 (t, 3H, $CH_3$), 4.29 (q, 2H, $CH_2CH_3$), 5.77 (s, 2H, $CH_2$), 7.30-7.32 (m, 2H, benzene H), 7.40-7.42 (m, 2H, benzene H), 7.49-7.52 (m, 1H, quinolinone $C_6$—H), 7.66-7.68 (m, 1H, quinolinone $C_8$—H), 7.72-7.74 (m, 1H, quinolinone $C_7$—H), 8.01 (s, 1H, butenoate $C_3$—H), 8.31-8.34 (m, 1H, quinolinone $C_5$—H), 9.14 (s, 1H, quinolinone $C_2$—H), 15.60 (bs, 1H, OH).

4-[1-(4-Hydroxyphenyl)methyl-1,4-dihydro-4-oxoquinolin-3-yl]-2,4-dioxobutanoic acid ethyl ester (RDS 2173). 64% yield; mp 179-181° C. (methanol). IR 3141 (OH), 1733 (CO ester), 1600 (CO ketone) $cm^{-1}$. $^1$H NMR (DMSO-$d_6$) δ 1.30 (t, 3H, $CH_3$), 4.31 (q, 2H, $CH_2CH_3$), 5.61 (s, 2H, $CH_2$), 6.71-6.73 (m, 2H, benzene H), 7.13-7.15 (m, 2H, benzene H), 7.41-7.50 (m, 1H, quinolinone $C_6$—H), 7.72-7.76 (m, 1H, quinolinone $C_7$—H), 7.78-7.80 (m, 1H, quinolinone $C_8$—H), 8.00 (s, 1H, butenoate $C_3$—H), 8.30-8.32 (m, 1H, quinolinone $C_5$—H), 9.06 (s, 1H, quinolinone $C_2$—H), 9.51 (bs, 1H, phenol OH), 14.00 (bs, 1H, OH).

4-[1-(2-Methoxyphenyl)methyl-1,4-dihydro-4-oxoquinolin-3-yl]-2,4-dioxobutanoic acid ethyl ester (RDS 2163). 98% yield; mp 154-156° C. (toluene). IR 1734 (CO ester), 1638 and 1602 (CO ketone) $cm^{-1}$. $^1$H NMR (DMSO-$d_6$) δ 1.28 (t, 3H, $CH_3CH_2$), 3.82 (s, 3H, $CH_3O$), 4.29 (q, 2H, $CH_2CH_3$), 5.63 (s, 2H, $CH_2$), 6.88-6.91 (m, 1H, benzene H), 7.06-7.08 (m, 1H, benzene H), 7.13-7.15 (m, 1H, benzene H), 7.29-7.33 (m, 1H, benzene H), 7.44-7.52 (m, 1H, quinolinone $C_6$—H), 7.71-7.76 (m, 2H, quinolinone $C_7$—H and $C_8$—H), 8.01 (s, 1H, butenoate $C_3$—H), 8.30-8.32 (m, 1H, quinolinone $C_5$—H), 9.05 (s, 1H, quinolinone $C_2$—H), 14.25 (bs, 1H, OH).

4-[1-(3-Methoxyphenyl)methyl-1,4-dihydro-4-oxoquinolin-3-yl]-2,4-dioxobutanoic acid ethyl ester (RDS 2160). 94% yield; mp 177-179° C. (toluene). IR 1729 (CO ester), 1628 and 1603 (CO ketone) $cm^{-1}$. $^1$H NMR (DMSO-$d_6$) δ 1.29 (t, 3H, $CH_3CH_2$), 3.70 (s, 3H, $CH_3O$), 4.29 (q, 2H, $CH_2CH_3$), 5.73 (s, 2H, $CH_2$), 6.71-6.73 (m, 1H, benzene H), 6.85-6.90 (m, 2H, benzene H), 7.22-7.26 (m, 1H, benzene H), 7.47-7.52 (m, 1H, quinolinone $C_6$—H), 7.70-7.75 (m, 2H, quinolinone $C_7$—H and $C_8$—H), 8.01 (s, 1H, butenoate $C_3$—H), 8.31-8.33 (m, 1H, quinolinone $C_5$—H), 9.11 (s, 1H, quinolinone $C_2$—H), 15.75 (bs, 1H, OH).

4-[1-(4-Methoxyphenyl)methyl-1,4-dihydro-4-oxoquinolin-3-yl]-2,4-dioxobutanoic acid ethyl ester (RDS 2034). 91% yield; mp 154-156° C. (methanol). IR 1734 (CO ester), 1638 and 1602 (CO ketone) $cm^{-1}$. $^1$H NMR (DMSO-$d_6$) δ 1.28 (t, 3H, $CH_3CH_2$), 3.68 (s, 3H, $CH_3O$), 4.29 (q, 2H, $CH_2CH_3$), 5.67 (s, 2H, $CH_2$), 6.89-6.91 (m, 2H, benzene H), 7.24-7.26 (m, 2H, benzene H), 7.48-7.52 (m, 1H, quinolinone $C_6$—H), 7.71-7.79 (m, 2H, quinolinone $C_7$—H and $C_8$—H), 8.00 (s, 1H, butenoate $C_3$—H), 8.29-8.32 (m, 1H, quinolinone $C_5$—H), 9.10 (s, 1H, quinolinone $C_2$—H), 15.60 (bs, 1H, OH).

4-[1-(4-Nitrophenyl)methyl-1,4-dihydro-4-oxoquinolin-3-yl]-2,4-dioxobutanoic acid ethyl ester (RDS 2017). 88% yield; mp 175-176° C. (toluene). IR 1718 (CO ester), 1638 and 1607 (CO ketone) cm$^{-1}$. $^1$H NMR (DMSO-$d_6$) δ 1.30 (t, 3H, $CH_3$), 4.32 (q, 2H, $CH_2CH_3$), 5.94 (s, 2H, $CH_2$), 7.46-7.54 (m, 3H, quinolinone $C_6$—H and benzene H), 7.59-7.61 (m, 1H, quinolinone $C_9$—H), 7.66-7.69 (m, 1H, quinolinone $C_7$—H), 8.02 (s, 1H, butenoate $C_3$—H), 8.18-8.20 (m, 2H, benzene H), 8.32-8.34 (m, 1H, quinolinone $C_5$—H), 9.18 quinolinone (s, 1H, $C_2$—H), 15.60 (bs, 1H, OH).

4-[1-(2,6-Difluorophenyl)methyl-1,4-dihydro-4-oxoquinolin-3-yl]-2,4-dioxobutanoic acid ethyl ester (RDS 1983). 92% yield; mp 172-173° C. (benzene/toluene). IR 3400 (OH), 1736 (CO ester), 1637 and 1602 (CO ketone) cm$^{-1}$. $^1$H NMR (DMSO-$d_6$) δ 1.29 (t, 3H, $CH_3$), 4.30 (q, 2H, $CH_2CH_3$), 5.85 (s, 2H, $CH_2$), 7.15-7.20 (m, 2H, benzene H), 7.45-7.54 (m, 2H, quinolinone $C_6$—H and benzene H), 7.66-7.69 (m, 1H, quinolinone $C_7$—H), 7.78-7.82 (m, 1H, quinolinone $C_8$—H), 7.99 (s, 1H, butenoate $C_3$—H), 8.28-8.32 (m, 1H, quinolinone $C_5$—H), 9.11 (s, 1H, quinolinone $C_2$—H), 15.50 (bs, 1H, OH).

4-[1-(4-Phenylbutyl)-1,4-dihydro-4-oxoquinolin-3-yl]-2,4-dioxobutanoic acid ethyl ester (RDS 1980). 76% yield; mp 88-90° C. (cyclohexane). IR 1716 (CO ester), 1635 and 1606 (CO ketone) cm$^{-1}$. $^1$H NMR (DMSO-$d_6$) δ 1.26 (t, 3H, $CH_3$), 1.58-1.65 (m, 2 □, C□$_2$), 1.75-1.77 (m, 2H, $CH_2$), 2.59 (t, 2H, $CH_2Ph$), 4.25 (q, 2H, $CH_2CH_3$), 4.47 (t, 2H, $CH_2N$), 7.12-7.25 (m, 5H, butenoate $C_3$—H and benzene H), 7.48-7.50 (m, 1H, quinolinone $C_6$—H), 7.74-7.78 (m, 2H, quinolinone $C_7$—H and $C_8$—H), 8.30-8.32 (m, 1H, quinolinone $C_5$—H), 8.77 (s, 1H, quinolinone $C_2$—H), 15.75 (bs, 2H, OH).

4-[α-(2-Naphthyl)methyl-1,4-dihydro-4-oxoquinolin-3-yl]-2,4-dioxobutanoic acid ethyl ester (RDS 1974). 78% yield; mp 153-154° C. (DMF/water). IR 3447 (OH), 1734 (CO ester), 1629 and 1603 (CO ketone) cm$^{-1}$. $^1$H NMR (DMSO-$d_6$) δ 1.28 (t, 3H, $CH_3$), 4.32 (q, 2H, $CH_2CH_3$), 5.94 (s, 2H, $CH_2$), 7.36-7.49 (m, 4H, naphthalene H), 7.66-7.775 (m, 2H, naphthalene H), 7.79 (s, 1H, naphthalene H), 7.84-7.92 (m, 3H, quinolinone $C_8$—H, $C_7$—H and $C_6$—H), 8.04 (s, 1H, butenoate $C_3$—H), 8.32 (m, 1H, quinolinone $C_5$—H), 9.20 (s, 1H, quinolinone $C_2$—H), 15.20 (bs, 1H, OH).

4-[1-(4-Pyridinyl)methyl-1,4-dihydro-4-oxoquinolin-3-yl]-2,4-dioxobutanoic acid ethyl ester (RDS 2085). 66% yield; mp 168-169° C. (DMF/water). IR 1717 (CO ester), 1645 (CO ketone) cm$^{-1}$. $^1$H NMR (DMSO-$d_6$) δ 1.28 (t, 3H, $CH_3$), 4.28 (q, 2H, $CH_2CH_3$), 5.82 (s, 2H, $CH_2$), 7.08 (m, 2H, pyridine H), 7.39 (m, 1H, quinolinone $C_6$—H), 7.55 (m, 1H, quinolinone $C_8$—H), 7.79 (m, 1H, quinolinone $C_7$—H), 7.95 (s, 1H, butenoate $C_3$—H), 8.32 (m, 1H, quinolinone $C_5$—H), 8.50 (m, 2H, pyridine H), 9.10 (s, 1H, quinolinone $C_2$—H), 15.50 (bs, 1H, OH).

4-[1-(2-Quinolinyl)methyl-1,4-dihydro-4-oxoquinolin-3-yl]-2,4-dioxobutanoic acid ethyl ester (RDS 1999). 100% yield; mp 237-238° C. (DMF/water). IR 3400 (OH), 1712 (CO ester), 1634 (CO ketone) cm$^{-1}$. $^1$H NMR (DMSO-$d_6$) δ 1.16 (m, 3H, $CH_3$), 4.30 (m, 2H, $CH_2CH_3$), 5.98 (s, 1H, $CH_2$), 7.11-7.94 (m, 9H, $C_6$—H, $C_7$—H, $C_8$—H quinolinone, butenoate $C_3$—H and quinoline H), 8.30 (m, 2H, quinolinone $C_5$—H and quinoline $C_5$—H), 9.04 (s, 1H, quinolinone $C_2$—H), 15.40 (bs, 1H, OH).

4-[1-(2-Fluorophenyl)methyl-7-chloro-1,4-dihydro-4-oxoquinolin-3-yl]-2,4-dioxobutanoic acid ethyl ester (RDS 2250). 80% yield; mp 173-175° C. (benzene). IR 1721 (CO ester), 1627 (CO ketone) cm$^{-1}$. $^1$H NMR (DMSO-$d_6$) δ 1.35 (t, 3H, $CH_3$), 4.35 (q, 2H, $CH_2CH_3$), 5.88 (s, 2H, $CH_2$), 7.22-7.26 (m, 1H, benzene H), 7.31-7.37 (m, 2H, benzene H), 7.43-7.48 (m, 1H, benzene H), 7.60-7.62 (m, 1H, quinolinone $C_6$—H), 7.90-7.92 (m, 1H, quinolinone $C_8$—H), 8.00 (s, 1H, butenoate $C_3$—H), 8.35-8.37 (m, 1H, quinolinone $C_5$—H), 9.12 (s, 1H, quinolinone $C_2$—H), 15.75 (bs, 1H, OH).

4-[1-(4-Fluorophenyl)methyl-6-fluoro-1,4-dihydro-4-oxoquinolin-3-yl]-2,4-dioxobutanoic acid ethyl ester (RDS 2077). 92% yield; mp 152-153° C. (toluene/cyclohexane). IR 1740 (CO ester), 1650 and 1624 (CO ketone) cm$^{-1}$. $^1$H NMR (DMSO-$d_6$) δ 1.29 (t, 3H, $CH_3$), 4.30 (q, 2H, $CH_2CH_3$), 5.78 (s, 2H, $CH_2$), 7.16-7.20 (m, 2H, benzene H), 7.29-7.37 (m, 2H, benzene H), 7.66 (m, 1H, quinolinone $C_7$—H), 7.81 (m, 1H, quinolinone $C_8$—H), 7.97 (m, 1H, quinolinone $C_5$—H) 8.00 (s, 1H, butenoate $C_3$—H), 9.13 (s, 1H, quinolinone $C_2$—H), 15.33 (bs, 1H, OH).

4-[1-(4-Fluorophenyl)methyl-7-fluoro-1,4-dihydro-4-oxoquinolin-3-yl]-2,4-dioxobutanoic acid ethyl ester (RDS 2021). 84% yield; mp 151-152° C. (benzene/cyclohexane). IR 1726 (CO ester), 1644 (CO ketone) cm$^{-1}$. $^1$H NMR (DMSO-$d_6$) δ 1.30 (t, 3H, $CH_3$), 4.30 (q, 2H, $CH_2CH_3$), 5.72 (s, 2H, $CH_2$), 7.17-7.21 (m, 2H, benzene H), 7.31-7.40 (m, 3H, benzene H and quinolinone $C_6$—H), 7.62 (m, 1H, quinolinone $C_8$—H) 7.97 (s, 1H, butenoate $C_3$—H), 8.36 (m, 1H, quinolinone $C_5$—H), 9.10 (s, 1H, quinolinone $C_2$—H), 14.00 (bs, 1H, OH).

4-[1-(4-Fluorophenyl)methyl-7-(1-pyrrolidinyl)-1,4-dihydro-4-oxoquinolin-3-yl]-2,4-dioxobutanoic acid ethyl ester (RDS 2196). 82% yield; mp 170 (dec)° C. (methanol). IR 3300 (OH), 1735 (CO ester), 1621 (CO ketone) cm$^{-1}$. $^1$H NMR (DMSO-$d_6$) δ 1.31 (t, 3H, $CH_3$), 1.98-2.10 (m, 4H, pyrrolidine H), 3.32-3.36 (m, 1H, pyrrolidine H), 4.30 (q, 2H, $CH_2CH_3$), 5.64 (s, 2H, $CH_2$), 6.37-6.39 (m, 1H, quinolinone $C_9$—H), 6.77-6.79 (m, 1H, quinolinone $C_6$—H), 7.29-7.32 (m, 2H, benzene H), 7.45-7.48 (m, 2H, benzene H),), 8.12-8.16 (m, 2H, quinolinone $C_5$—H and butenoate $C_3$—H), 8.79 (s, 1H, quinolinone $C_2$—H), 13.50 (bs, 1H, OH).

4-[1-(4-Fluorophenyl)methyl-8-fluoro-1,4-dihydro-4-oxoquinolin-3-yl]-2,4-dioxobutanoic acid ethyl ester (RDS 2107). 83% yield; mp 179-180° C. (benzene/cyclohexane). IR 3300 (OH), 1744 (CO acid), 1648 and 1604 (CO ketone) cm$^{-1}$. $^1$H NMR (DMSO-$d_6$) δ 1.27 (t, 3H, $CH_3$), 4.30 (q, 2H, $CH_2CH_3$), 5.78 (s, 2H, $CH_2$), 7.14-7.24 (m, 4H, benzene H), 7.48-7.53 (m, 1H, quinolinone $C_6$—H), 7.59-7.69 (m, 1H, quinolinone $C_7$—H) 7.97 (s, 1H, butenoate $C_3$—H), 8.17-8.19 (m, 1H, quinolinone $C_5$—H), 9.01 (s, 1H, quinolinone $C_2$—H), 15.50 (bs, 1H, OH).

4-[1-(4-Fluorophenyl)methyl-8-chloro-1,4-dihydro-4-oxoquinolin-3-yl]-2,4-dioxobutanoic acid ethyl ester (RDS 2111). 98% yield; mp 164-165° C. (toluene). IR 3400 (OH), 1749 (CO ester), 1644 (CO ketone) cm$^{-1}$. $^1$H NMR (DMSO-$d_6$) δ 1.29 (t, 3H, $CH_3$), 4.30 (q, 2H, $CH_2CH_3$), 6.09 (s, 2H, $CH_2$), 7.14-7.16 (m, 4H, benzene H), 7.15 (m, 1H, quinolinone $C_6$—H), 7.82 (m, 1H, quinolinone $C_7$—H), 7.91 (s, 1H, butenoate $C_3$—H), 8.34 (m, 1H, quinolinone $C_5$—H), 8.81(s, 1H, quinolinone $C_2$—H), 15.25 (bs, 1H, OH).

4-[1-(4-Fluorophenyl)methyl-6,7-dichloro-1,4-dihydro-4-oxoquinolin-3-yl]-2,4-dioxobutanoic acid ethyl ester (RDS 2187). 98% yield; mp 144-145° C. (toluene/cyclohexane). IR 1727 (CO ester), 1638 (CO ketone) cm$^{-1}$. $^1$H NMR (DMSO-$d_6$) δ 1.35 (t, 3H, $CH_3$), 4.38 (q, 2H, $CH_2CH_3$), 5.82 (s, 2H, $CH_2$), 7.18-7.30 (m, 2H, benzene H), 7.43-7.46 (m, 2H, benzene H), 7.98 (s, 1H, butenoate $C_3$—H), 8.14 (s, 1H, quinolinone $C_8$—H), 8.41 (s, 1H, quinolinone $C_5$—H), 9.14 (s, 1H, quinolinone $C_2$—H), 16.00 (bs, 1H, OH).

Quinolinyl 2,4-Dioxobutanoic Acids 4-(1-Phenylmethyl-1,4-dihydro-4-oxoquinolin-3-yl)-2,4-dioxobutanoic acid (RDS 1993). 82% yield; mp 141-142° C. (DMF/water). IR 3424 (OH), 1726 (CO acid), 1625 (CO ketone) cm$^{-1}$. $^1$H NMR (DMSO-d$_6$) δ 5.75 (s, 2H, CH$_2$), 7.22-7.36 (m, 5H, benzene H), 7.42-7.48 (m, 1H, quinolinone C$_6$—H), 7.65-7.70 (m, 2H, quinolinone C$_7$—H and C$_8$—H), 7.90 (s, 1H, butenoate C$_3$—H), 8.30-8.32 (m, 2H, quinolinone C$_5$—H), 9.08 (s, 1H, quinolinone C$_2$—H), 16.00 (bs, 2H, OH).

4-[1-(2-Fluorophenyl)methyl-1,4-dihydro-4-oxoquinolin-3-yl]-2,4-dioxobutanoic acid (RDS 1990). 83% yield; mp 172-174° C. (toluene). IR 3400 (OH), 1748 (CO acid), 1621 (CO ketone) cm$^{-1}$. $^1$H NMR (DMSO-d$_6$) δ 5.81 (s, 2H, CH$_2$), 7.14-7.28 (m, 3H, benzene H), 7.35-7.50 (m, 2H, quinolinone C$_6$—H and benzene H), 7.70-7.74 (m, 2H, quinolinone C$_7$—H and C$_8$—H), 7.95 (s, 1H, butenoate C$_3$—H), 8.31-8.33 (m, 1H, quinolinone C$_5$—H), 9.08 (s, 1H, quinolinone C$_2$—H), 15.00 (bs, 2H, OH).

4-[1-(3-Fluorophenyl)methyl-1,4-dihydro-4-oxoquinolin-3-yl]-2,4-dioxobutanoic acid (RDS 1987). 60% yield; mp 158-159° C. (washed with anhydrous ethanol). IR 3392 (OH), 1720 (CO acid), 1630 (CO ketone) cm$^{-1}$. $^1$H NMR (DMSO-d$_6$) δ 5.76 (s, 2H, CH$_2$), 7.05-7.18 (m, 3H, benzene H), 7.26-7.48 (m, 2H, quinolinone C$_6$—H and benzene H), 7.66-7.69 (m, 2H, quinolinone C$_7$—H and C$_8$—H), 8.03 (s, 1H, butenoate C$_3$—H), 8.29-8.31 (m, 1H, quinolinone C$_5$—H), 9.08 (s, 1H, quinolinone C$_2$—H), 15.75 (bs, 2H, OH).

4-[1-(4-Chlorophenyl)methyl-1,4-dihydro-4-oxoquinolin-3-yl]-2,4-dioxobutanoic acid (RDS 2012). 96% yield; mp 177-179° C. (washed with anhydrous ethanol). IR 3400 (OH), 1700 (CO acid), 1630 (CO ketone) cm$^{-1}$. $^1$H NMR (DMSO-d$_6$) δ 5.76 (s, 2H, CH$_2$), 7.29-7.31 (m, 2H, benzene H), 7.39-7.41 (m, 2H, benzene H), 7.48-7.51 (m, 1H, quinolinone C$_6$—H), 7.65-7.67 (m, 1H, quinolinone C$_8$—H), 7.70-7.73 (m, 1H, quinolinone C$_7$—H), 7.97 (s, 1H, butenoate C$_3$—H), 8.30-8.32 (m, 1H, quinolinone C$_5$—H), 9.11 (s, 1H, quinolinone C$_2$—H), 15.53 (bs, 2H, OH).

4-[1-(4-Hydroxyphenyl)methyl-1,4-dihydro-4-oxoquinolin-3-yl]-2,4-dioxobutanoic acid (RDS 2174). 77% yield; mp 206-208° C. (washed with hot isopropanol). IR 3135 (OH), 1718 (CO acid), 1600 (CO ketone) cm$^{-1}$. $^1$H NMR (DMSO-d$_6$) δ 5.59 (s, 2H, CH$_2$), 6.71-6.73 (m, 2H, benzene H), 7.11-7.13 (m, 2H, benzene H), 7.46-7.49 (m, 1H, quinolinone C$_6$—H), 7.67-7.78 (m, 2H, quinolinone C$_7$—H and C$_9$—H), 7.92 (s, 1H, butenoate C$_3$—H), 8.28-8.30 (m, 1H, quinolinone C$_5$—H), 9.00 (s, 1H, quinolinone C$_2$—H), 9.50 (bs, 1H, phenol OH), 14.00 (bs, 2H, OH).

4-[1-(2-Methoxyphenyl)methyl-1,4-dihydro-4-oxoquinolin-3-yl]-2,4-dioxobutanoic acid (RDS 2164). 94% yield; mp 173-175° C. (washed with hot isopropanol). IR 3400 (OH), 1728 (CO acid), 1620 and 1611 (CO ketone) cm$^{-1}$. $^1$H NMR (DMSO-d$_6$) δ 3.82 (s, 3H, CH$_3$), 5.68 (s, 2H, CH$_2$), 6.86-6.90 (m, 1H, benzene H), 7.01-7.08 (m, 1H, benzene H), 7.11-7.13 (m, 1H, benzene H), 7.29-7.32 (m, 1H, benzene H), 7.43-7.50 (m, 1H, quinolinone C$_6$—H), 7.71-7.75 (m, 2H, quinolinone C$_7$—H and C$_8$—H), 7.95 (s, 1H, butenoate C$_3$—H), 8.29-8.31 (m, 1H, quinolinone C$_5$—H), 9.02 (s, 1H, quinolinone C$_2$—H), 15.00 (bs, 2H, OH).

4-[1-(3-Methoxyphenyl)methyl-1,4-dihydro-4-oxoquinolin-3-yl]-2,4-dioxobutanoic acid (RDS 2161). 80% yield; mp 179-181° C. (washed with isopropanol). IR 3400 (OH), 1748 (CO acid), 1630 and 1602 (CO ketone) cm$^{-1}$. $^1$H NMR (DMSO-d$_6$) δ 3.70 (s, 3H, CH$_3$), 5.65 (s, 2H, CH$_2$), 6.70-6.72 (m, 1H, benzene H), 6.85-6.89 (m, 2H, benzene H), 7.22-7.26 (m, 1H, benzene H), 7.45-7.51 (m, 1H, quinolinone C$_6$—H), 7.66-7.74 (m, 2H, quinolinone C$_7$—H and C$_8$—H), 7.98 (s, 1H, butenoate C$_3$—H), 8.30-8.32 (m, 1H, quinolinone C$_5$—H), 9.09 (s, 1H, quinolinone C$_2$—H), 15.00 (bs, 2H, OH).

4-[1-(4-Methoxyphenyl)methyl-1,4-dihydro-4-oxoquinolin-3-yl]-2,4-dioxobutanoic acid (RDS 2035). 100% yield; mp 149-150° C. (washed with anhydrous ethanol). IR 3400 (OH), 1726 (CO acid), 1620 and 1611 (CO ketone) cm$^{-1}$. $^1$H NMR (DMSO-d$_6$) δ 3.69 (s, 3H, CH$_3$), 5.66 (s, 2H, CH$_2$), 6.89 (m, 2H, benzene H), 7.24-7.26 (m, 2H, benzene H), 7.44-7.50 (m, 1H, quinolinone C$_6$—H), 7.70-7.78 (m, 2H, quinolinone C$_7$—H and C$_8$—H), 7.93 (s, 1H, butenoate C$_3$—H), 8.29-8.31 (m, 1H, quinolinone C$_5$—H), 9.07 (s, 1H, quinolinone C$_2$—H), 15.15 (bs, 2H, OH).

4-[1-(4-Nitrophenyl)methyl-1,4-dihydro-4-oxoquinolin-3-yl]-2,4-dioxobutanoic acid (RDS 2018). 90% yield; mp 230-232° C. (washed with anhydrous ethanol). IR 3100 (OH), 1731 (CO acid), 1634 and 1602 (CO ketone) cm$^{-1}$. $^1$H NMR (DMSO-d$_6$) δ 5.87 (s, 2H, CH$_2$), 7.45-7.52 (m, 3H, quinolinone C$_6$—H and benzene H), 7.57-7.59 (m, 1H, quinolinone C$_8$—H), 7.67-7.69 (m, 1H, quinolinone C$_7$—H), 7.92 (s, 1H, butenoate C$_3$—H), 8.18-8.20 (m, 2H, benzene H), 8.31-8.33 (m, 1H, quinolinone C$_5$—H), 9.12 (s, 1H, quinolinone C$_2$—H), 15.00 (bs, 2H, OH).

4-[1-(2,6-Difluorophenyl)methyl-1,4-dihydro-4-oxoquinolin-3-yl]-2,4-dioxobutanoic acid (RDS 1984). 64% yield; mp 171-172° C. (washed with anhydrous ethanol). IR 3600 (OH), 1748 (CO acid), 1620 (CO ketone) cm$^{-1}$. $^1$H NMR (DMSO-d$_6$) δ 5.82 (s, 2H, CH$_2$), 7.14-7.18 (m, 2H, benzene H), 7.47-7.49 (m, 2H, quinolinone C$_6$—H and benzene H), 7.66-7.68 (m, 1H, quinolinone C$_7$—H), 7.76-7.78 (m, 1H, quinolinone C$_8$—H), 7.88 (s, 1H, butenoate C$_3$—H), 8.29-8.31 (m, 1H, quinolinone C$_5$—H), 9.06 (s, 1H, quinolinone C$_2$—H), 15.00 (bs, 2H, OH).

4-[1-(4-Phenylbutyl)-1,4-dihydro-4-oxoquinolin-3-yl]-2,4-dioxobutanoic acid (RDS 1981). 100% yield; mp 136-138° C. (DMF/water). IR 3400 (OH), 1747 (CO acid), 1623 and 1603 (CO ketone) cm$^{-1}$. $^1$H NMR (DMSO-d$_6$) δ 1.61-1.66 (m, 2H, CH$_2$), 1.72-1.82 (m, 2H, CH$_2$), 2.60 (t, 2H, CH$_2$Ph), 4.47 (t, 2H, CH$_2$N), 7.12-7.25 (m, 6H, butenoate C$_3$—H and benzene H), 7.47-7.53 (m, 1H, quinolinone C$_6$—H), 7.78-7.83 (m, 2H, quinolinone C$_7$—H and C$_8$—H), 8.30-8.32 (m, 1H, quinolinone C$_5$—H), 8.86 (s, 1H, quinolinone C$_2$—H), 15.00 (bs, 1H, OH).

4-[1-(2-Naphthyl)methyl-1,4-dihydro-4-oxoquinolin-3-yl]-2,4-dioxobutanoic acid (RDS 1975). 50% yield; mp 212-213° C. (washed with anhydrous ethanol). IR 3400 (OH), 1710 (CO acid), 1638 (CO ketone) cm$^{-1}$. $^1$H NMR (DMSO-d$_6$) δ 5.89 (s, 2H, CH$_2$), 7.38-7.49 (m, 4H, naphthalene H), 7.64-7.75 (m, 3H, naphthalene H), 7.85-7.91 (m, 2H, quinolinone C$_7$—H and C$_8$—H), 7.97 (s, 1H, butenoate C$_3$—H), 8.30-8.32 (m, 1H, quinolinone C$_5$—H), 9.14 (s, 1H, quinolinone C$_2$—H), 16.00 (bs, 2H, OH).

4-[1-(4-Pyridinyl)methyl-1,4-dihydro-4-oxoquinolin-3-yl]-2,4-dioxobutanoic acid (RDS 2086). 66% yield; mp>300° C. (DMSO/water). IR 3240 (OH), 1700 (CO acid), 1600 (CO ketone) cm$^{-1}$. $^1$H NMR (DMSO-d$_6$) δ 5.79 (s, 2H, CH$_2$), 7.18 (m, 2H, pyridine H), 7.45-7.66 (m, 3H, quinolinone C$_8$—H, C$_7$—H and C$_6$—H), 7.98 (s, 1H, butenoate C$_3$—H), 8.33 (m, 1H, quinolinone C$_5$—H), 8.51 (m, 2H, pyridine H), 9.12 (s, 1H, quinolinone C$_2$—H), 14.00 (bs, 2H, OH).

4-[1-(2-Quinolinyl)methyl-1,4-dihydro-4-oxoquinolin-3-yl]-2,4-dioxobutanoic acid (RDS 2000). 62% yield; mp>300° C. (DMF/water). IR 3400 (OH), 1700 (CO acid), 1633 (CO ketone) cm$^{-1}$. $^1$H NMR (DMSO-d$_6$) δ 5.98 (s, 2H, CH$_2$), 7.40-7.48 (m, 1H, quinoline C$_6$—H), 7.47-7.49 (m, 1H, quinoline C$_4$—H), 7.55-7.62 (m, 2H, quinoline C$_7$—H and C$_6$—H), 7.68-7.72 (m, 1H, quinolinone C$_7$—H), 7.81-7.83 (m, 1H, quinoline C$_8$—H), 7.93-7.95 (m, 2H, quinolinone C$_8$—H and butenoate C$_3$—H), 8.30-8.32 (m, 1H, quinoline C$_5$—H), 8.38-8.40 (m, 1H, quinolinone C$_5$—H), 8.94 (s, 1H, quinolinone C$_2$—H), 17.00 (bs, 2H, OH).

4-[1-(2-Fluorophenyl)methyl-7-chloro-1,4-dihydro-4-oxoquinolin-3-yl]-2,4-dioxobutanoic acid (RDS 2251). 82% yield; mp 187-189° C. (washed with isopropanol). IR 3400 (OH), 1732 (CO acid), 1621 (CO ketone) cm$^{-1}$. $^1$H NMR (DMSO-d$_6$) δ 5.88 (s, 2H, CH$_2$), 7.22-7.36 (m, 3H, benzene H), 7.44-7.46 (m, 1H, benzene H), 7.59-7.62 (m, 2H, quinolinone C$_6$—H), 7.70-7.74 (m, 2H, quinolinone C$_7$—H and C$_8$—H), 7.90 (s, 1H, butenoate C$_3$—H), 8.35-8.37 (m, 1H, quinolinone C$_5$—H), 9.10 (s, 1H, quinolinone C$_2$—H), 15.00 (bs, 2H, OH).

4-[1-(4-Fluorophenyl)methyl-6-fluoro-1,4-dihydro-4-oxoquinolin-3-yl]-2,4-dioxobutanoic acid (RDS 2078). 95% yield; mp 183-184° C. (washed with anhydrous ethanol). IR 3100 (OH), 1730 (CO acid), 1613 (CO ketone) cm$^{-1}$. $^1$H NMR (DMSO-d$_6$) δ 5.76 (s, 2H, CH$_2$), 7.16-7.20 (m, 2H, benzene H), 7.33-7.36 (m, 2H, benzene H), 7.65 (m, 1H, quinolinone C$_7$—H), 7.80 (m, 1H, quinolinone C$_9$—H), 7.94-7.97 (m, 2H, quinolinone C$_5$—H and butenoate C$_3$—H), 9.10 (s, 1H, quinolinone C$_2$—H), 14.67 (bs, 2H, OH).

4-[1-(4-Fluorophenyl)methyl-7-fluoro-1,4-dihydro-4-oxoquinolin-3-yl]-2,4-dioxobutanoic acid (RDS 2022). 95% yield; mp 162-163° C. (washed with anhydrous ethanol). IR 3300 (OH), 1719 (CO acid), 1635 (CO ketone) cm$^{-1}$. $^1$H NMR (DMSO-d$_6$) δ 5.70 (s, 2H, CH$_2$), 7.14-7.21 (m, 2H, benzene H), 7.31-7.37 (m, 3H, benzene H and, quinolinone C$_6$—H), 7.60 (m, 1H, quinolinone C$_8$—H) 7.93 (s, 1H, butenoate C$_3$—H), 8.34 (m, 1H, quinolinone C$_5$—H), 9.05 (s, 1H, quinolinone C$_2$—H), 14.60 (bs, 2H, OH).

4-[1-(4-Fluorophenyl)methyl-7-(1-pyrrolidinyl)-1,4-dihydro-4-oxoquinolin-3-yl]-2,4-dioxobutanoic acid (RDS 2197). 87% yield; mp 197-199° C. (washed with isopropanol). IR 3300 (OH), 1718 (CO acid), 1614 (CO ketone) cm$^{-1}$. $^1$H NMR (DMSO-d$_6$) δ 2.06-2.13 (m, 4H, pyrrolidine H), 3.26-3.30 (m, 4H, pyrrolidine H), 5.77 (s, 2H, CH$_2$), 6.42-6.45 (m, 1H, quinolinone C$_8$—H), 6.81-6.85 (m, 1H, quinolinone C$_6$—H), 7.18-7.25 (m, 2H, benzene H), 7.49-7.52 (m, 2H, benzene H), 8.02 (s, 1H, butenoate C$_3$—H), 8.15-8.17 (m, 1H, quinolinone C$_5$—H), 9.09 (s, 1H, quinolinone C$_2$—H), 14.00 (bs, 2H, OH).

4-[1-(4-Fluorophenyl)methyl-8-fluoro-1,4-dihydro-4-oxoquinolin-3-yl]-2,4-dioxobutanoic acid (RDS 2108). 78% yield; mp 180-181° C. (washed with hot anhydrous ethanol). IR 3300 (OH), 1732 (CO acid), 1634 and 1602 (CO ketone) cm$^{-1}$. $^1$H NMR (DMSO-d$_6$) δ 5.86 (s, 2H, CH$_2$), 7.12-7.23 (m, 4H, benzene H), 7.45-7.50 (m, 1H, quinolinone C$_6$—H), 7.57-7.62 (m, 1H, quinolinone C$_7$—H) 7.70 (s, 1H, butenoate C$_3$—H), 8.16-8.18 (m, 1H, quinolinone C$_5$—H), 8.96 (s, 1H, quinolinone C$_2$—H), 14.30 (bs, 2H, OH).

4-[1-(4-Fluorophenyl)methyl-8-chloro-1,4-dihydro-4-oxoquinolin-3-yl]-2,4-dioxobutanoic acid (RDS 2112). 82% yield; mp 175-177° C. (washed with anhydrous ethanol). IR 3300 (OH), 1742 (CO acid), 1637 and 1603 (CO ketone) cm$^{-1}$. $^1$H NMR (DMSO-d$_6$) δ 6.08 (s, 2H, CH$_2$), 7.00-7.30 (m, 4H, benzene H), 7.44-7.46 (m, 1H, quinolinone C$_6$—H), 7.81-7.83 (m, 2H, butenoate C$_3$—H and quinolinone C$_7$—H), 8.33-8.35 (m, 1H, quinolinone C$_5$—H), 8.89 (s, 1H, quinolinone C$_2$—H), 14.70 (bs, 2H, OH).

4-[1-(4-Fluorophenyl)methyl-6,7-dichloro-1,4-dihydro-4-oxoquinolin-3-yl]-2,4-dioxobutanoic acid (RDS 2188). 86% yield; mp 175-177° C. (washed with isopropanol). IR 3300 (OH), 1722 (CO acid), 1630 (CO ketone) cm$^{-1}$. $^1$H NMR (DMSO-d$_6$) δ 5.75 (s, 2H, CH$_2$), 7.17-7.22 (m, 2H, benzene H), 7.32-7.39 (m, 2H, benzene H), 7.88 (s, 1H, quinolinone C$_8$—H), 8.06 (s, 1H, butenoate C$_3$—H), 8.32 (s, 1H, quinolinone C$_5$—H), 9.05 (s, 1H, quinolinone C$_2$—H), 16.00 (bs, 2H, OH).

EXAMPLE 4

Integrase Assays

Figure 1:
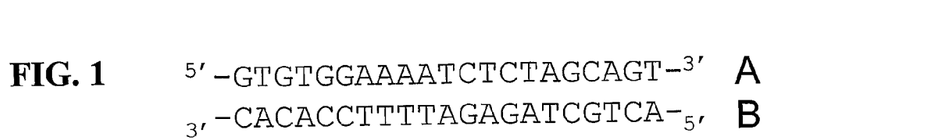
FIG. 1 represents the oligonucleotides employed in the reaction scheme shown in FIG. 2 for an in vitro integration assay.

Several of the compounds disclosed herein were tested for their ability to inhibit HIV-1 integrase in vitro. In the assay, a 21-mer double-stranded DNA oligonucleotide (oligonucleotide *A 5'-end-labeled annealed to oligonucleotide B; see FIG. 1), corresponding to the last 21 bases of the U5 viral LTR, is used to follow both the 3'-processing and the 3'-end joining (strand transfer) steps of the integration reaction. Oligonucleotide A is 5'-end-labeled by T4-Polynucleotide Kinase (Gibco BRL/Life Technologies, Rockville, Md.). 10 pmoles of oligonucleotide A is incubated at 37° C. for 30 minutes in 50 µl of 1×kinase buffer containing 10 µCi of γ-ATP (Amersham Pharmacia Biotech, Piscataway, N.J.) and 10 units of kinase. The labeling solution is then applied to the top of a G25 Quick Spin column (Boehringer Mannheim, Indianapolis, Ind.) and the filtrate annealed with 20 pmoles of oligonucleotide B (complementary strand) for 5 minutes at 95° C. and 30 minutes at 37° C.

Figure 2:
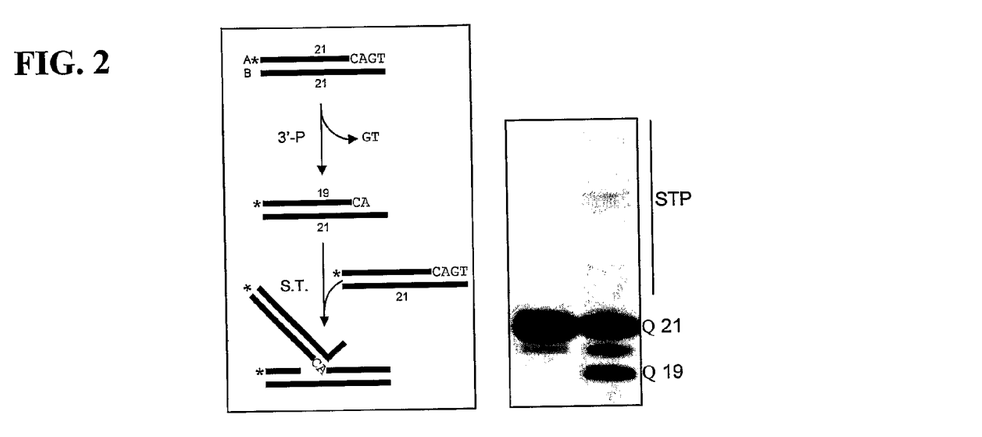

In the 3'-processing reaction, integrase liberates a GT dinucleotide at the 3'-end of the labeled strand resulting in the generation of a 19-mer labeled product. The strand transfer (3'-end joining) reaction consists in the insertion of a 3'-processed oligonucleotide into another DNA target. This strand transfer step leads to higher and lower molecular weight species migrating slower and faster respectively, than the original 21-mer substrate (FIG. 2). The higher molecular weight species (STP) are generally used to evaluate strand transfer (integration).

For inhibitor testing, a DNA-enzyme complex is preformed by mixing 500 mM of HIV-1 integrase and 5 nM of 5'-labeled double-stranded DNA template (*A/B) in a buffer containing 50 mM MOPS, pH 7.2, 7.5 mM MgCl$_2$ and 14.3 mM β-mercaptoethanol for 15 minutes on ice. The integration reaction is then initiated by addition of the drug and continued in a total volume of 10 µl for 30 minutes at 37° C. The reaction is stopped by adding the same volume of electrophoresis denaturing dye containing 99% formamide (Sigma-Aldrich, Milwaukee, Wis.), 1% SDS, 0.2 mg/ml bromophenol blue (Sigma-Aldrich, Milwaukee, Wis.) and 0.2 mg/ml xylene cyanol blue (Sigma-Aldrich, Milwaukee, Wis.). Samples are loaded on 20% 19/1 acrylamide denaturing gel Accugel (National Diagnostics, Atlanta, Ga.) containing 7 M urea (Gibco BRL/Life Technologies, Rockville, Md.) in 1× TBE (Gibco BRL/Life Technologies, Rockville, Md.). Gels were exposed overnight and analyzed using a Molecular Dynamics Phosphorimager (Sunnyvale, Calif.).

Figure 3:
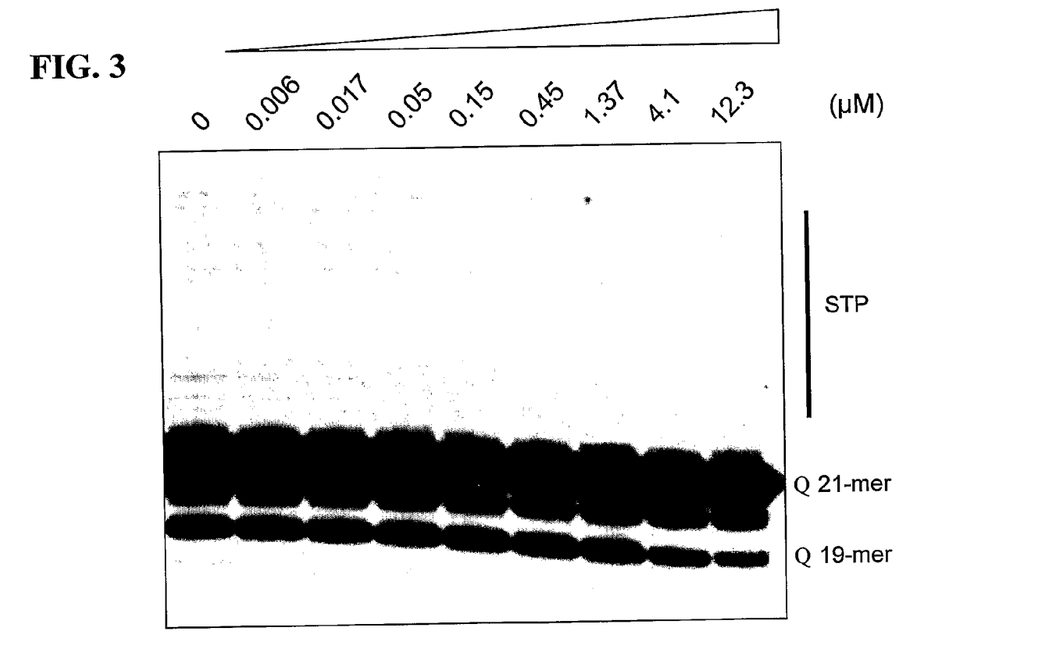
FIG. 3 depicts the results of an in vitro integration assay.

Diketo acids have been described previously to inhibit selectively the strand transfer step of the integration reaction. See Hazuda et al., "Inhibitors of strand transfer that prevent integration and inhibit HIV-1 replication in cells," Science 287:646-650, 2000. A typical experiment corresponding to the inhibition of HIV-1 integrase by increasing concentrations of compound RDS1792 (FIG. 3), reveals an IC$_{50}$ of 0.11 µM for the strand transfer reaction whereas, the IC$_{50}$ for 3'-processing is 4 µM. Results are summarized below in Table 3. Among the compounds that were tested, the diketo acid derivative RDS1625 is the most potent compound against HIV-1 integrase in vitro with an IC$_{50}$ value of approximately 50 nM for strand transfer.

TABLE 3

In vitro inhibition of HIV-1 integrase

| Compound | IC50 3'-Processing (μM) | IC50 Strand transfer (μM) |
|---|---|---|
| RDS1624 | >12.3 | 1.757 |
| RDS1625 | 1.8 | 0.047 |
| RDS1787 | 6.4 | 0.403 |
| RDS1792 | 4.0 | 0.110 |
| RDS1675 | >100 | >100 |
| RDS1680 | >100 | >100 |
| RDS1754 | >100 | >100 |
| RDS1786 | >100 | >100 |
| RDS1793 | >1000 | >1000 |
| RDS1794 | >100 | >100 |
| RDS2077 | >37 | 0.49 |
| RDS2078 | 2.9 | 0.047 |
| RDS1755 | >100 | >100 |
| RDS1787 | 28.7 | 0.124 |
| RDS2021 | 25 | 1.9 |
| RDS2022 | 1.9 | 0.042 |
| RDS1788 | >100 | >100 |
| RDS1792 | 14 | 0.0210 |
| RDS1996 | 40 | 0.34 |
| RDS1997 | 0.20 | 0.012 |
| RDS1980 | >333 | 120 |
| RDS1981 | >333 | <0.45 |
| RDS1974 | >333 | 32 |
| RDS1975 | 18 | <0.45 |
| RDS1999 | >1000 | 3.5 |
| RDS2000 | 70 | 0.40 |
| RDS1992 | >1000 | 0.70 |
| RDS1993 | 4.0 | 0.034 |
| RDS1989 | 125 | 0.28 |
| RDS1990 | 1.2 | 0.016 |
| RDS1986 | >12.3 | 4.9 |
| RDS1987 | 4.6 | 0.015 |
| RDS1624 | >100 | 0.326 |
| RDS1625 | 2.20 | 0.0313 |
| RDS2011 | >37 | >37 |
| RDS2012 | 22 | 0.54 |
| RDS2034 | >37 | >37 |
| RDS2035 | 28 | 0.51 |
| RDS2017 | >37 | >37 |
| RDS2018 | 27 | 0.64 |
| RDS1983 | >12.3 | 0.25 |
| RDS1984 | 0.7 | 0.019 |

The results in Table 3 show that oxoquinolines that are substituted with a diketo group show significant anti-integrase activity (e.g., an $IC_{50}$ strand transfer of not greater than 1.757 μm). One of the most potent of the tested compounds (RDS1625) is substituted with a single diketo acid group at the 3-position on the oxoquinoline ring. Another of the most potent of the tested compounds (RDS1997) is substituted with two diketo acid groups. In general, the compounds listed in Table 3 that include a diketo acid substituent exhibited superior anti-integrase activity compared to the compounds that include a diketo ester substituent.

EXAMPLE 5

HIV Antiviral Activity

Several of the compounds disclosed herein were tested for their ability to inhibit HIV cell multiplication. The compounds were solubilized in dimethyl sulfoxide at 200 mM and then diluted into culture medium. MT-4, C8166, H9/III$_B$ cells were grown at 37° C. in a 5% $CO_2$ atmosphere in RPMI 1640 medium, supplemented with 10% fetal calf serum (FCS), 100 IU/mL penicillin G and 100 μg/mL streptomycin. Cell cultures were checked periodically for the absence of mycoplasma contamination with a MycoTect Kit (Gibco). Human immunodeficiency viruses type-1 (HIV-1, III$_B$ strain) were obtained from supernatants of persistently infected H9/IIIB. HIV-1 stock solutions had titres of $4.5 \times 10^6$ 50% cell culture infectious dose ($CCID_{50}$)/mL. Titration of HIV-1 was performed in C8166 cells by the standard limiting dilution method (dilution 1:2, four replica wells/dilution) in 96-well plates. The infectious virus titer was determined by light microscope scoring of cytopathicity after 4 days of incubation and the virus titers were expressed as $CCID_{50}$/mL.

Activity of the compounds against HIV-1 multiplication in acutely infected cells was based on the inhibition of virus-induced cytopathicity in MT-4 cells. Briefly, 50 μL of culture medium containing $1 \times 10^4$ cells were added to each well of flat-bottom microtiter trays containing 50 μL of culture medium with or without various concentrations of the test compounds. Then 20 μL of an HIV-1 suspension containing 100 $CCID_{50}$ was added. After a 4-day incubation at 37° C., the number of viable cells was determined by the 3-(4,5-dimethylthiazol-1-yl)-2,5-diphenyltetrazolium bromide (MTT) method (Pauwels, R.; Balzarini, J.; Baba, M.; Snoeck, R.; Schols, D.; Herdewijn, P.; Desmyster, J.; De Clercq, E. *J. Virol. Methods* 1988, 20, 309-321). Cytotoxicity of the compounds was evaluated in parallel with their antiviral activity, and was based on the viability of mock-infected cells, as monitored by the MTT method. The 50% effective concentration value ($EC_{50}$) values for the compounds were as follows: RDS 1625 was 40 μM; RDS 1624 was 3.5 μM; and RDS 1755 was 5 μM.

Having illustrated and described the principles of the disclosed compounds, compositions and methods, it will be apparent that these compounds, compositions and methods may be modified in arrangement and detail without departing from such principles.

What is claimed is:

1. A compound of the following formula (I), or a tautomer or pharmaceutically acceptable salt thereof:

wherein $R_1$ is selected from —H, —$C_{1-6}$ alkyl, or —$C_{1-6}$ alkyl substituted with $R_7$;

Z is selected from —C(O)O$R_2$ or —C(O)CH$_2$C(O)X;

X is selected from:
(a) a 5 or 6-membered aromatic or heteroaromatic ring, containing 0, 1, 2, 3 or 4 heteroatoms selected from oxygen, nitrogen and sulfur, unsubstituted or independently substituted on a nitrogen or carbon atom by at least one substituent selected from halogen, $C_{1-6}$ alkyl, or phenyl, or
(b) —C(O)O$R_2$;

$R_2$ is selected from —H or —$C_{1-6}$ alkyl;

$R_3$, $R_4$, $R_5$ and $R_6$ are each independently selected from —H, —halogen, —$C_{1-6}$alkyloxy—, —N($R_8$)($R_9$), —C(O)CH$_3$, —C(O)CH$_2$C(O)X, —S(O)$_n$—$R_{10}$ wherein n is independently selected from 0, 1 and 2, heteroalkyl, cycloalkyl, substituted cycloalkyl, heterocycloalkyl, substituted heterocycloalkyl, aryl, substituted aryl, heteroaryl, or substituted heteroaryl;

$R_7$ independently selected from heteroalkyl, cycloalkyl, substituted cycloalkyl, heterocycloalkyl, substituted heterocycloalkyl, aryl, substituted aryl, heteroaryl, or substituted heteroaryl;

each $R_8$ and $R_9$ is independently selected from —H or —$C_{1-2}$ alkyl; and each $R_{10}$ is independently selected from —$C_{1-6}$ alkyl, pyridyl, or phenyl, wherein the phenyl is unsubstituted or substituted on a carbon atom by least one substituent selected from halogen, —$CH_3$, —$OR_2$, or —$NO_2$;

provided that if Z is —C(O)$OR_2$ then at least one of $R_3$, $R_4$, $R_5$ or $R_6$ is —C(O)$CH_2$C(O)X.

2. The compound of claim 1, wherein Z is —C(O)$CH_2$C(O)X and $R_3$, $R_4$, $R_5$ and $R_6$ are not —C(O)$CH_2$C(O)X.

3. The compound of claim 2, wherein X is —C(O)$OR_2$.

4. The compound of claim 3, wherein $R_2$ is —H or ethyl; $R_3$ and $R_6$ are each —H; $R_4$ and $R_5$ are each independently —H or -halo; and $R_1$ is 4-fluorophenylmethyl.

5. The compound of claim 3, wherein $R_2$ is —H or alkyl; and $R_1$ is 4-fluorophenylmethyl.

6. The compound of claim 1, wherein $R_7$ is independently selected from pyridyl, thienyl, naphthyl or phenyl, wherein the phenyl is unsubstituted or independently substituted on a carbon atom by at least one substituent selected from halogen, —$CH_3$, —$OR_2$, or —$NO_2$.

7. The compound of claim 1, wherein Z is —C(O)$CH_2$C(O)C(O)$OR_2$ and $R_1$ is —$C_{1-6}$ alkyl, or $C_{1-6}$ alkyl substituted with $R_7$.

8. The compound of claim 4, wherein $R_2$, $R_4$ and $R_5$ are each —H.

9. The compound of claim 4, wherein $R_2$ is —H and $R_4$ and $R_5$ are each —H or —Cl wherein at least one of $R_4$ or $R_5$ is —Cl.

10. The compound of claim 7, wherein $R_1$ is a halogen-substituted arylalkyl.

11. The compound of claim 1, wherein Z is —C(O)$OR_2$ and at least one of $R_3$, $R_4$, $R_5$ or $R_6$ is —C(O)$CH_2$C(O)X.

12. The compound of claim 11, wherein $R_4$ is —C(O)$CH_2$C(O)X.

13. The compound of claim 12, wherein $R_1$ is a halogen-substituted arylalkyl.

14. The compound of claim 13, wherein $R_4$ is —C(O)$CH_2$C(O)C(O)$OR_2$, $R_2$ is —H or ethyl, and $R_1$ is 4-fluorophenylmethyl.

15. The compound of claim 1, wherein at least one of $R_3$, $R_4$, $R_5$ and $R_6$ is a 5 or 6-membered heteroalicyclic ring containing 1 or 2 nitrogen heteroatoms.

16. A pharmaceutical composition comprising the formula (I) compound of claim 1, and a pharmaceutically acceptable carrier.

17. A pharmaceutical composition comprising the formula (I) compound of claim 4, and a pharmaceutically acceptable carrier.

18. A pharmaceutical composition comprising the formula (I) compound of claim 11, and a pharmaceutically acceptable carrier.

19. A method of treating HIV infection in a subject, the method comprising administering to the subject a therapeutically effective amount of at least one formula (I) compound of claim 1.

20. The method of claim 19, wherein the method of treatment helps to delay progression of infection by HIV.

21. The method of claim 19, comprising orally administering the formula (I) compound.

22. The method of claim 19, comprising parenterally, sublingually, intranasally, intrathecally, topically, opthalmically or rectally administering the formula (I) compound.

23. The method of claim 19, wherein the formula (I) compound comprises a compound wherein Z is —C(O)$CH_2$C(O)X and $R_3$, $R_4$, $R_5$ and $R_6$ are not —C(O)$CH_2$C(O)X.

24. The method of claim 23, wherein the formula (I) compound comprises a compound wherein X is —C(O)$OR_2$.

25. The method of claim 24, wherein the formula (I) compound comprises a compound wherein $R_2$ is —H or ethyl; $R_3$ and $R_6$ are each —H; $R_4$ and $R_5$ are each independently —H or -halo; and $R_1$ is 4-fluorophenylmethyl.

26. The method of claim 19 wherein the formula (I) compound comprises a compound wherein Z is —C(O)$OR_2$ and at least one of $R_3$, $R_4$, $R_5$ or $R_6$ is —C(O)$CH_2$C(O)X.

27. The method of claim 26 wherein the formula (I) compound comprises a compound wherein $R_4$ is —C(O)$CH_2$C(O)C(O)$OR_2$, $R_2$ is —H or ethyl, and $R_1$ is 4-fluorophenylmethyl.

28. A method of inhibiting a retroviral integrase, the method comprising exposing the HIV integrase to an integrase inhibiting amount of at least one formula (I) compound of claim 1.

29. The method of claim 28, wherein the formula (I) compound comprises a compound wherein Z is —C(O)$CH_2$C(O)X and $R_3$, $R_4$, $R_5$ and $R_6$ are not —C(O)$CH_2$C(O)X.

30. The method of claim 29, wherein the formula (I) compound comprises a compound wherein X is —C(O)$OR_2$.

31. The method of claim 30, wherein the formula (I) compound comprises a compound wherein $R_2$ is —H or ethyl; $R_3$ and $R_6$ are each —H; $R_4$ and $R_5$ are independently —H or -halo; and $R_1$ is 4-fluorophenylmethyl.

32. The method of claim 28 wherein the formula (I) compound comprises a compound wherein Z is —C(O)$OR_2$ and at least one of $R_3$, $R_4$, $R_5$ and $R_6$ is —C(O)$CH_2$C(O)X.

33. The method of claim 32 wherein the formula (I) compound comprises a compound wherein $R_4$ is —C(O)$CH_2$C(O)C(O)$OR_2$, $R_2$ is —H or ethyl, and $R_1$ is 4-fluorophenylmethyl.

34. The method of claim 28, comprising inhibiting a HIV integrase.

35. The method of claim 28, comprising inhibiting strand transfer catalyzed by HIV integrase.

36. The method of claim 28, comprising inhibiting incorporation of a donor strand DNA into a receiving strand DNA.

37. A method of treating HIV infection in a subject, the method comprising administering to the subject a therapeutically effective amount of a pharmaceutical composition of claim 16.

38. A method of treating HIV infection in a subject, the method comprising administering to the subject a therapeutically effective amount of a pharmaceutical composition of claim 17.

39. A method of treating HIV infection in a subject, the method comprising administering to the subject a therapeutically effective amount of a pharmaceutical composition of claim 18.

40. The compound of claim 1, wherein Z is —C(O)$CH_2$C(O)C(O)$OR_2$; $R_2$ is —H or —$CH_2CH_3$; $R_3$, $R_4$ and $R_6$ are each —H; $R_5$ is 1-pyrrolidinyl; and $R_1$ is 4-fluorophenylmethyl.

41. The compound of claim 1, wherein Z is —C(O)$CH_2$C(O)C(O)$OR_2$; $R_2$ is —H or —$CH_2CH_3$; $R_3$ and $R_6$ are each —H; $R_4$ is —H or —Halo; and $R_5$ is —H, -halo, or a 5 or 6-membered heteroalicyclic ring containing 1 or 2 nitrogen heteroatoms.

42. A pharmaceutical composition comprising the formula (I) compound of claim 40, and a pharmaceutically acceptable carrier.

* * * * *